(12) United States Patent
Blanc

(10) Patent No.: US 10,589,161 B2
(45) Date of Patent: *Mar. 17, 2020

(54) SYSTEM AND METHOD FOR MONITORING PERFORMANCE CHARACTERISTICS ASSOCIATED WITH USER ACTIVITIES INVOLVING SWINGING INSTRUMENTS

(71) Applicant: Arccos Golf, LLC, Stamford, CT (US)

(72) Inventor: Fabrice Claude Blanc, Stamford, CT (US)

(73) Assignee: Arccos Golf, LLC, Stamford, CT (US)

( * ) Notice: Subject to any disclaimer, the term of this patent is extended or adjusted under 35 U.S.C. 154(b) by 179 days.

This patent is subject to a terminal disclaimer.

(21) Appl. No.: 15/714,235

(22) Filed: Sep. 25, 2017

(65) Prior Publication Data

US 2018/0015349 A1 Jan. 18, 2018

Related U.S. Application Data

(63) Continuation of application No. 14/804,752, filed on Jul. 21, 2015, now Pat. No. 9,770,639.

(51) Int. Cl.
*A63B 69/36* (2006.01)
*A61B 5/00* (2006.01)
(Continued)

(52) U.S. Cl.
CPC ........ *A63B 69/3641* (2013.01); *A61B 5/1122* (2013.01); *A61B 5/6895* (2013.01);
(Continued)

(58) Field of Classification Search
CPC ........ A63B 69/3641; A63B 2069/3602; A63B 2220/00; A63B 2102/32; G06K 9/00342; A61B 5/1122; A61B 5/6895
(Continued)

(56) References Cited

U.S. PATENT DOCUMENTS 5,332,225 A * 7/1994 Ura .................... A63B 69/3685
473/223
5,507,485 A * 4/1996 Fisher .................... A63B 69/36
473/131
(Continued)

OTHER PUBLICATIONS

U.S. Appl. No. 15/312,500, filed Nov. 18, 2016, US 2017-0087431 A1.
(Continued)

*Primary Examiner* — Nini F Legesse
(74) *Attorney, Agent, or Firm* — McCarter & English, LLP

(57) ABSTRACT

Exemplary embodiments of the present disclosure are directed to various components of a system for monitoring and/or tracking a user's performance during an activity involving an instrument that is swung. Exemplary embodiments can include a sensor module configured to be secured to and/or embedded within the instrument. The sensor module can detect a swing event and/or an impact between the instrument and an object and can generate pressures waves that propagate through air. The pressure waves can include information or represent information about a use of the instrument and can be detected by an electronic device associated with the user, which can display the information, process the information, and/or transmit the information to a remote system. The pressure waves can be modulated to encode information within the pressure waves.

23 Claims, 22 Drawing Sheets

(51) Int. Cl.
  *A61B 5/11* (2006.01)
  *G06K 9/00* (2006.01)
  *A63B 102/32* (2015.01)

(52) U.S. Cl.
  CPC .. *G06K 9/00342* (2013.01); *A63B 2069/3602* (2013.01); *A63B 2102/32* (2015.10); *A63B 2220/00* (2013.01)

(58) Field of Classification Search
  USPC ........ 473/131, 219, 221–223, 226, 227, 409
  See application file for complete search history.

(56) References Cited

U.S. PATENT DOCUMENTS

| | | |
|---|---|---|
| 5,528,248 A | 6/1996 | Steiner et al. |
| 5,565,845 A | 10/1996 | Hara |
| 5,616,832 A * | 4/1997 | Nauck ............... A63B 60/42 73/65.03 |
| 5,685,786 A | 11/1997 | Dudley |
| 5,699,244 A | 12/1997 | Clark, Jr. et al. |
| 5,740,077 A | 4/1998 | Reeves |
| 5,966,135 A | 10/1999 | Roy et al. |
| 6,024,655 A | 2/2000 | Coffee et al. |
| 6,045,364 A * | 4/2000 | Dugan ............... A63B 69/0024 434/252 |
| 6,118,376 A | 11/2000 | Regester |
| 6,261,102 B1 * | 7/2001 | Dugan ............... A63B 69/0024 434/252 |
| 6,282,362 B1 | 8/2001 | Murphy et al. |
| 6,299,553 B1 | 10/2001 | Petuchowski |
| 6,324,473 B1 | 11/2001 | Eschenbach |
| 6,366,205 B1 | 4/2002 | Sutphen |
| 6,441,745 B1 | 8/2002 | Gates |
| 6,456,938 B1 * | 9/2002 | Barnard ............... A63B 57/00 701/454 |
| 6,520,864 B1 | 2/2003 | Wilk |
| 6,537,076 B2 * | 3/2003 | McNitt ............... A63B 24/0003 434/247 |
| 6,582,328 B2 | 6/2003 | Kuta et al. |
| 6,697,820 B1 | 2/2004 | Tarlie |
| 6,753,778 B2 | 6/2004 | Kruger |
| 6,905,339 B2 * | 6/2005 | DiMare ............... A63B 69/36 434/247 |
| 7,010,550 B2 | 3/2006 | Tarlie |
| 7,118,498 B2 * | 10/2006 | Meadows ............... A63B 57/00 473/407 |
| 7,121,962 B2 * | 10/2006 | Reeves ............... A63B 71/0669 473/407 |
| 7,254,516 B2 | 8/2007 | Case et al. |
| 7,264,554 B2 * | 9/2007 | Bentley ............... A61B 5/1122 473/222 |
| 7,603,255 B2 | 10/2009 | Case et al. |
| 7,789,742 B1 * | 9/2010 | Murdock ............ A63B 24/0021 463/3 |
| 7,800,480 B1 * | 9/2010 | Joseph ............... A63B 24/0021 340/10.1 |
| 7,801,575 B1 | 9/2010 | Balardeta et al. |
| 7,804,404 B1 | 9/2010 | Balardeta et al. |
| 7,831,212 B1 | 11/2010 | Balardeta et al. |
| 7,847,693 B1 | 12/2010 | Balardeta et al. |
| 7,853,211 B1 | 12/2010 | Balardeta et al. |
| 7,883,427 B1 | 2/2011 | Balardeta et al. |
| 7,883,428 B1 | 2/2011 | Balardeta et al. |
| 7,894,286 B2 | 2/2011 | Jung et al. |
| 7,899,408 B1 | 3/2011 | Balardeta et al. |
| 7,911,186 B1 | 3/2011 | Balardeta et al. |
| 7,915,865 B1 | 3/2011 | Balardeta et al. |
| 7,922,606 B2 | 4/2011 | Balardeta et al. |
| 7,927,225 B1 | 4/2011 | Balardeta et al. |
| 7,941,097 B1 | 5/2011 | Balardeta et al. |
| 7,942,762 B2 | 5/2011 | Balardeta et al. |
| 7,946,926 B1 | 5/2011 | Balardeta et al. |
| 7,979,030 B1 | 7/2011 | Balardeta et al. |
| 8,016,690 B2 | 9/2011 | Rushe |
| 8,070,628 B2 | 12/2011 | Denton et al. |
| 8,113,967 B1 | 2/2012 | Seluga et al. |
| 8,120,332 B2 | 2/2012 | Balardeta et al. |
| 8,137,208 B2 | 3/2012 | Ahem et al. |
| 8,142,302 B2 | 3/2012 | Balardeta et al. |
| 8,142,304 B2 | 3/2012 | Reeves |
| 8,147,335 B2 | 4/2012 | Kim et al. |
| D659,787 S | 5/2012 | Balardeta et al. |
| 8,172,702 B2 | 5/2012 | Meadows et al. |
| 8,192,293 B2 | 6/2012 | Denton et al. |
| 8,202,148 B2 | 6/2012 | Young |
| 8,210,959 B2 | 7/2012 | Balardeta et al. |
| 8,221,269 B2 | 7/2012 | Meadows et al. |
| 8,226,495 B2 | 7/2012 | Savarese et al. |
| 8,272,970 B2 | 9/2012 | Balardeta et al. |
| 8,337,335 B2 | 12/2012 | Dugan |
| 8,355,869 B2 | 1/2013 | Balardeta et al. |
| 8,364,293 B2 | 1/2013 | Doherty et al. |
| 8,409,024 B2 | 4/2013 | Marty et al. |
| 8,430,762 B2 | 4/2013 | Balardeta et al. |
| 8,430,770 B2 | 4/2013 | Dugan |
| 8,444,499 B2 | 5/2013 | Balardeta et al. |
| 8,446,255 B2 | 5/2013 | Balardeta et al. |
| 8,460,111 B2 | 6/2013 | Hart |
| 8,465,376 B2 | 6/2013 | Bentley |
| 8,523,711 B2 | 9/2013 | Meadows et al. |
| 8,529,380 B1 | 9/2013 | Hubenthal et al. |
| 8,535,170 B2 | 9/2013 | Reeves |
| 8,556,752 B2 | 10/2013 | Meadows et al. |
| 8,620,463 B2 | 12/2013 | Doherty et al. |
| 8,624,738 B2 | 1/2014 | Savarese et al. |
| 8,647,214 B2 | 2/2014 | Wiegers |
| 8,655,462 B2 | 2/2014 | Sanders |
| 8,668,595 B2 | 3/2014 | Boyd et al. |
| 8,696,482 B1 | 4/2014 | Pedenko et al. |
| 8,708,841 B2 | 4/2014 | Doherty et al. |
| 8,758,152 B2 | 6/2014 | Hall |
| 8,758,170 B2 | 6/2014 | Reeves |
| 8,764,576 B2 | 7/2014 | Takasugi |
| 8,808,102 B2 | 8/2014 | Dugan |
| 8,808,114 B2 | 8/2014 | Dugan |
| 8,831,905 B2 | 9/2014 | Papadourakis |
| 8,840,483 B1 | 9/2014 | Steusloff et al. |
| 8,840,484 B2 | 9/2014 | Parke et al. |
| 8,845,459 B2 | 9/2014 | Balardeta et al. |
| 8,870,673 B2 | 10/2014 | Beno et al. |
| 8,894,502 B2 | 11/2014 | Rose |
| 8,926,445 B2 | 1/2015 | Davenport |
| 8,933,967 B2 | 1/2015 | Huston et al. |
| 8,979,665 B1 | 3/2015 | Najafi et al. |
| 8,986,129 B2 | 3/2015 | Miettinen et al. |
| 8,986,130 B2 | 3/2015 | Hatton et al. |
| 8,989,441 B2 | 3/2015 | Han et al. |
| 9,005,047 B2 | 4/2015 | Savarese et al. |
| 9,022,870 B2 | 5/2015 | Jeffery et al. |
| 9,050,519 B1 | 6/2015 | Ehlers et al. |
| 9,095,761 B2 | 8/2015 | Trenkle et al. |
| 9,186,546 B2 | 11/2015 | Boyd et al. |
| 9,199,177 B2 | 12/2015 | Knapp et al. |
| 9,375,624 B2 | 6/2016 | Boyd et al. |
| 9,393,478 B2 | 7/2016 | Niegowski |
| 9,403,072 B2 | 8/2016 | Baker et al. |
| 9,403,073 B2 | 8/2016 | McDonnell et al. |
| 9,409,071 B1 | 8/2016 | Beno et al. |
| 9,433,844 B2 | 9/2016 | Boyd et al. |
| 9,535,162 B2 | 1/2017 | Park |
| 9,630,079 B2 | 4/2017 | Davenport |
| 9,646,199 B2 | 5/2017 | Bose et al. |
| 9,649,532 B2 | 5/2017 | Case |
| 9,656,134 B2 | 5/2017 | Meadows et al. |
| 9,656,147 B2 | 5/2017 | Reeves |
| 9,731,182 B2 | 8/2017 | Dugan |
| 9,770,639 B2 | 9/2017 | Blanc |
| 9,789,361 B2 | 10/2017 | Beno et al. |
| 9,916,001 B2 | 3/2018 | Thurman et al. |
| 9,925,439 B2 | 3/2018 | Baker et al. |
| 9,943,744 B2 | 4/2018 | Meadows et al. |
| 9,968,826 B2 | 5/2018 | McDonnell et al. |

(56) References Cited

U.S. PATENT DOCUMENTS

| | | |
|---|---|---|
| 9,968,827 B2 | 5/2018 | Beno et al. |
| 2002/0115047 A1 | 8/2002 | McNitt et al. |
| 2002/0188359 A1 | 12/2002 | Morse |
| 2004/0121849 A1 | 6/2004 | Curkovic et al. |
| 2005/0032582 A1 | 2/2005 | Mahajan et al. |
| 2005/0227791 A1 | 10/2005 | McCreary et al. |
| 2006/0148594 A1 | 7/2006 | Saintoyant et al. |
| 2006/0178110 A1 | 8/2006 | Nurminen et al. |
| 2007/0129178 A1 | 6/2007 | Reeves |
| 2009/0017944 A1 | 1/2009 | Savarese et al. |
| 2009/0209358 A1 | 8/2009 | Niegowski |
| 2010/0149331 A1 | 6/2010 | DiMare et al. |
| 2011/0230986 A1 | 9/2011 | Lafortune et al. |
| 2011/0301435 A1 | 12/2011 | Albert et al. |
| 2012/0088544 A1 | 4/2012 | Bentley et al. |
| 2012/0238381 A1 | 9/2012 | Denton et al. |
| 2012/0289354 A1 | 11/2012 | Cottam et al. |
| 2012/0322569 A1 | 12/2012 | Cottam |
| 2013/0095939 A1 | 4/2013 | Meadows et al. |
| 2013/0144411 A1 | 6/2013 | Savarese et al. |
| 2013/0150121 A1 | 6/2013 | Jeffery et al. |
| 2013/0267335 A1 | 10/2013 | Boyd et al. |
| 2013/0267336 A1 | 10/2013 | Boyd et al. |
| 2014/0018181 A1 | 1/2014 | Blake et al. |
| 2014/0018195 A1 | 1/2014 | Meadows et al. |
| 2014/0172132 A1 | 6/2014 | Ura |
| 2014/0221118 A1 | 8/2014 | Meadows et al. |
| 2014/0244012 A1 | 8/2014 | Doherty et al. |
| 2014/0274240 A1 | 9/2014 | Meadows |
| 2014/0277630 A1 | 9/2014 | Meadows et al. |
| 2014/0278207 A1 | 9/2014 | Hadden et al. |
| 2014/0315660 A1 | 10/2014 | Edmonson et al. |
| 2014/0336989 A1 | 11/2014 | Ye et al. |
| 2015/0068616 A1 | 3/2015 | Early et al. |
| 2015/0080011 A1 | 3/2015 | Zelinka et al. |
| 2015/0100245 A1 | 4/2015 | Huang et al. |
| 2015/0105172 A1 | 4/2015 | Thurman et al. |
| 2015/0141005 A1 | 5/2015 | Suryavanshi et al. |
| 2017/0216705 A1 | 4/2017 | Reeves |

OTHER PUBLICATIONS

U.S. Appl. No. 15/872,601, filed Jan. 16, 2018, US 2018-0200605 A1.

PCT Search Report and Written Opinion for PCT/US2015/031668 dated Aug. 10, 2015.

U.S. Appl. No. 14/804,752, filed Jul. 21, 2015, now U.S. Pat. No. 9,770,639.

* cited by examiner

SYSTEM AND METHOD FOR MONITORING PERFORMANCE CHARACTERISTICS ASSOCIATED WITH USER ACTIVITIES INVOLVING SWINGING INSTRUMENTS

CROSS REFERENCE TO RELATED APPLICATIONS

This application is a continuation of U.S. patent application Ser. No. 14/804,752, filed on Jul. 21, 2015, the disclosure of which is incorporated by reference herein in its entirety.

BACKGROUND

In recent years, there has been efforts to automate the monitoring, tracking, and/or analysis of a golfer's performance during a round of golf. There remains a need for a system that effectively communicates information and facilitates reliable and accurate automated monitoring, tracking, and/or analysis of a golfer's performance during a round of golf.

SUMMARY

Exemplary embodiments of the present disclosure are directed to various components of systems, methods, and/or non-transitory computer-readable media that facilitate monitoring and/or tracking a user's performance during a sporting activity involving a swinging instrument.

In accordance with embodiments of the present disclosure, a sensor module encoded with an identification parameter and adapted to be affixed to or embedded in a golf club is disclosed. The sensor module includes sensor circuitry, an electromechanical device, and control circuitry. The sensor circuitry includes at least one sensor that is operable to generate an output in response to usage of the golf club (e.g., a golf swing). The electromechanical device is operable to generate a pressure wave that propagates through air. The control circuitry is operatively coupled to the sensor circuitry and the electromechanical device. The control circuitry is configured to (i) detect whether there is an impact between the golf club and an object during the golf swing based on the output of the sensor circuitry, (ii) control the electromechanical device to generate the pressure wave in response to detection of the impact, and (iii) control the electromechanical device to modulate the pressure wave to encode the identification parameter in the pressure wave and to indicate that the impact has been detected.

In accordance with embodiments of the present disclosure, an electronic device for monitoring tracking of a golf game is disclosed. The electronic device includes an electroacoustic device and control circuitry. The electroacoustic transducer operable to sense a pressure wave propagating through air and convert the pressure wave into an electrical signal. The pressure wave being generated by a sensor module affixed to or embedded within a golf club in response to detection of an impact between the golf club and an object during a golf swing, and is modulated to encode therein information including an identification parameter associated with the sensor module and to indicate detection of the impact. The control circuitry is operable to (i) receive the electrical signal, (ii) extract the identification parameter from the electrical signal, (iii) associate the pressure wave with the golf club, and (iv) attribute the impact to the golf club.

In accordance with embodiments of the present disclosure, a system for monitoring activity associated with a golf club is disclosed. The system includes a sensor module affixed to or embedded in a golf club and an electronic device spaced away from the sensor module. The sensor module include sensor circuitry having at least one sensor that is operable to generate an output in response to usage of the golf club (e.g., a golf swing), an electromechanical device operable to generate a pressure wave that propagates through air; and control circuitry. The control circuitry is operatively coupled to the sensor circuitry and the electromechanical device, and is configured to (i) detect whether there is an impact between the golf club and an object during the golf swing based on the output of the sensor circuitry, (ii) control the electromechanical device to output the pressure wave in response to detection of the impact, and (iii) control the electromechanical device to modulate the pressure wave to encode the identification parameter in the pressure wave and to indicate that the impact has been detected. The electronic device includes an electroacoustic transducer operable to sense the pressure wave propagating through air and convert the pressure wave into an electrical signal; and control circuitry operable to (i) receive the electrical signal, (ii) extract the identification parameter from the electrical signal, (iii) associate the pressure wave with the golf club, and (iv) attribute the impact to the golf club.

In accordance with embodiments of the present disclosure, a method of monitoring a golf club for a golf shot is disclosed. The method includes sensing, via sensor circuitry of a sensor module, usage of a golf club (e.g., a golf swing); and detecting, via control circuitry, whether there is an impact between the golf club and an object during the golf swing based on an output of the sensor circuitry. The method also includes controlling an electromechanical device of the sensor module to generate, in response to detection of the impact, a modulated pressure wave having encoded therein information including an identification parameter and indicating detection of the impact. The modulated pressure wave propagates through air to a remote electronic device configured to associate the pressure wave with the golf club based on the identification parameter.

In accordance with embodiments of the present disclosure, the pressure wave can convey swing analysis information to the remote electronic device.

In accordance with embodiments of the present disclosure, the identification parameter can be effective to differentiate the golf club from which the pressure wave propagates from other golf clubs. For example, the remote electronic device can be programmed to differentiate between a plurality of golf clubs based on the identification parameter.

In accordance with embodiments of the present disclosure, the pressure wave includes at least one characteristic of a swing of the golf club.

In accordance with embodiments of the present disclosure, the electromechanical device includes a speaker for generating the pressure wave.

In accordance with embodiments of the present disclosure, the pressure wave can have a frequency between approximately fifteen kilohertz and approximately twenty-five kilohertz.

In accordance with exemplary embodiments, a frequency at which the pressure wave propagates uniquely identifies the golf club.

In accordance with embodiments of the present disclosure, the control circuitry can include a processing device.

In accordance with embodiments of the present disclosure, the sensor circuitry can include an accelerometer. A change in the acceleration of the golf club sensed by the accelerometer can be detected as corresponding to the impact between the golf club and an object.

In accordance with exemplary embodiments, the control circuitry of the remote electronic device demodulates the electrical signal corresponding to the pressure wave.

In accordance with embodiments of the present disclosure, the electronic device can include a non-transitory computer-readable medium storing instructions executable by a processing device included in the control circuitry. The processing device can be programmed to execute the instructions to detect and extract the information from the electrical signal corresponding to the pressure wave.

In accordance with embodiments of the present disclosure, the electronic device can include a global positioning system (GPS) receiver to receive broadcasts from a global positioning satellite. The processing device of the electronic device can be programmed to determine a geographic location at which the electronic device senses the pressure wave.

Any combination and/or permutation of embodiments is envisioned. Other embodiments, objects, and features will become apparent from the following detailed description considered in conjunction with the accompanying drawings. It is to be understood, however, that the drawings are designed as an illustration only and not as a definition of the limits of the present disclosure.

DESCRIPTION OF EXEMPLARY EMBODIMENTS

Exemplary embodiments of the present disclosure are directed to various components of systems, methods, and non-transitory computer-readable media for monitoring and/or tracking a user's performance during an activity involving one or more swinging instruments. Exemplary embodiments can include sensor modules configured to be secured of fixed to the instruments. As a non-limiting example, exemplary embodiments of the present disclosure can detect swing events and/or impacts between the instruments and objects, can identify false positives to distinguish between swing events that should be attributed to a user's performance and swing event that should not be attributed to a user's performance, can implement power management features to limit or manage a power consumption of the sensor module, and/or can implement other features, operations, function, and/or processes described herein.

The sensor module can create pressure waves that propagate through air. The pressure waves can be detected by an electroacoustic transducer of an electronic device, which converts the mechanical energy of the pressure waves into electrical signals for processing by the electronic device. In exemplary embodiments, the pressure wave can include information that can be used to identify the instrument from which the pressure wave propagates and can include information about a use of the instrument. The information included in the pressure wave can be extracted by the electronic device upon detection of the pressure wave and conversion of the pressure wave to electrical signals.

Figure 1:
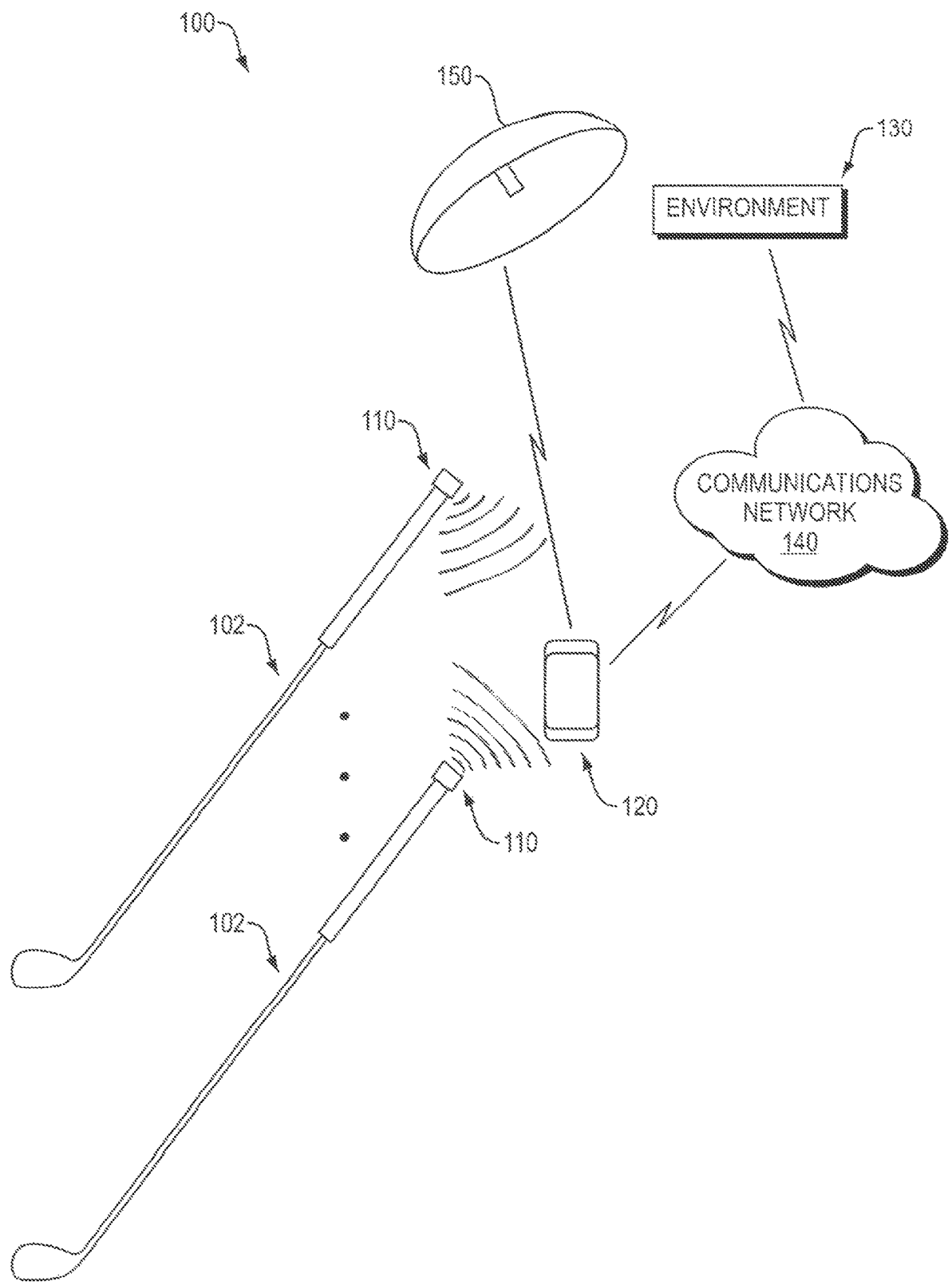
FIG. 1 depicts a performance monitoring system in accordance with exemplary embodiments of the present disclosure.

FIG. 1 depicts an exemplary performance monitoring system 100 that can be implemented using hardware, software, and/or a combination thereof. The system 100 can track and/or analyze user performance associated with a user activity involving one or more instruments 102 (e.g., golf clubs) that are swung by the user during the activity (e.g., a round of golf). The system 100 can include sensor modules 110 secured or fixed to the instruments 102 and electronic devices 120 (e.g., mobile phones, tablets, laptops, etc.) that are configured to communicate with one or more of the sensor modules 110. In some embodiments, the system 100 can include a remote user system 130 that can be accessible by users via a communications network 140 as described in more detail herein.

The one or more instruments 102 can be, for example, golf clubs, bats (e.g., baseball, softball, cricket), hockey sticks (e.g., field and/or ice hockey sticks), racquets (e.g., tennis, squash, racquet ball, badminton, ping pong, and/or any other types of racquets), long handled mallets (e.g., polo, croquet, and/or any other types of mallets), and/or any other suitable instruments that may be swung by a user during a sporting activity, recreational activity, leisure activity, occupational activity, and the like.

In exemplary embodiments, each sensor modules 110 can detect when a user is preparing to swing a corresponding one of the instruments 102, can detect when the instruments is being swung, and/or can detect when the instrument strikes an object. The sensor module 110 can use this information to compute and/or identify performance characteristics associated with the user's use of the instruments 102. For embodiments in which the sensor modules compute and/or identify the performance characteristics related to the swing, the sensor modules 110 can create pressure waves that propagate through the air and include information associated with the performance characteristics. The one or more of the electronic devices 120 can detect the pressure waves and can extract the information from the pressure waves, which can be used by the one or more electronic devices to monitor and/or track a user's performance during an activity. As one example, in some embodiments, the sensor modules 110 can detect and/or identify performance characteristics including when the instruments 102 are swung, acceleration information associated with the swing, whether the instrument hits another object, and/or whether the swing and impact correspond to a swing that should or should not be counted as a shot (e.g., a golf shot), and can create a pressure wave that includes this information as described herein.

In some embodiments, the pressure waves created by the sensor modules 110 can be used to identify the sensor module from which the pressure waves propagate. For example, in some embodiments, the sensor modules 110 can create a pressure waves having a specified frequencies that are different from each other such that the frequency of the pressure waves can be used to identify the sensor module from which a pressure wave propagates (e.g., one sensor module can create a pressure wave having a first frequency, another sensor module can create a pressure wave having a second frequency, still another sensor module can create a pressure wave having a second frequency, and so on).

Additionally, the presence or absence of a pressure wave can be used by the electronic device to identify information corresponding to a use of the instrument 102. For example, the sensor modules 110 can be configured to create a fixed, single frequency pressure wave after detecting an impact between the instruments 102 and an object. Absence of the pressure is an indication that the sensor modules 110 have not detected an impact. Upon detection of a pressure wave, the electronic device can identify that the sensor module 110 from which the pressure propagates and can determine that the sensor module detected an impact based on the presence/existence of the pressure wave.

In some embodiments, each sensor module 110 can be associated with a unique identifier. For example, in exemplary embodiments the unique identifiers can be identification parameters stored in the storage/memory of the sensor modules 110 (e.g., represented as a string of binary values). The sensor modules 110 can include the unique identifiers in pressure waves and the one or more electronic devices 120 extract the unique identifiers from the pressures waves to associate the pressure waves with their corresponding sensor modules. As one example, the sensor modules can modulate the pressure waves to encode the unique identifiers in the pressure waves and the electronic device(s) 120 can decode electrical signals corresponding to converted mechanical energy of the modulated pressure waves to extract the unique identifiers. Because the sensors modules 110 can encode the unique identifiers in the pressure waves, the pressures waves can be created to have the same or substantially similar (base/carrier) frequency.

The sensor modules 110 can be modulated to encode the pressure waves with information corresponding to the use of the instruments 102 to which the sensor modules 110 are affixed or within which the sensor modules 110 are embedded. As one example, after detecting an impact between the instrument 102 and an object, the sensor module 110 can create a modulated pressure wave (e.g., using amplitude modulation, phase modulation, and/or frequency modulation) having encoded therein an indication that the sensor module 110 detected an impact. Upon detection of this modulated pressure wave, the electronic device(s) can decode the modulated pressure wave and determine that the sensor module detected an impact based on processing of electrical signals derived from the decoded pressure wave.

The one or more electronic devices 120 can use the performance characteristics to monitor and/or track the user's performance during an activity, and to render one or more graphical user interfaces to display the performance characteristics as well as other data maintained, generated, and/or received by the one or more electronic devices 120. For example, the one or more electronic devices 120 can be programmed and/or configured to identify a location of the user when one of the instruments 102 is swung and/or contacts an object (e.g., a ball, the ground, or any other object) during a swing. In exemplary embodiments, the location of the electronic devices 120 (e.g., a longitude and latitude) can be determined using a global positioning system (GPS) receiver within the electronic devices 120 that is in communication with a GPS satellite 150.

In exemplary embodiments, the one or more electronic devices 120 can be programmed and/or configured to associate the pressure waves and/or unique identifiers of each of the sensor modules 110 with a corresponding one of the instruments 102 to which the sensor modules are affixed or within which the sensor modules 110 are embedded such that when the one or more electronic devices 120 detects a pressure wave propagating from one of the sensor modules 110, the one or more electronic devices 120 can determine which of the instruments 102 was used. For example, in exemplary embodiments, the sensor modules 110 and the electronic device(s) 120 can be configured to be associated such that each of the sensor modules 110 can be recognized by the one or more electronic devices 120. During a recognition process, one of the sensor modules 110 affixed to or embedded within one of the instruments 102 can be instructed to create a pressure wave (e.g., having a specified frequency or being modulated to encode a unique identifier) and the one or more electronic devices 120 can be instructed to detect the pressure wave, upon detection of the pressure wave, the electronic device can be programmed to associate a parameter or characteristic of the pressure wave (e.g., a frequency of the pressure wave or a unique identifier encoded in the pressure wave) with the instrument to which the sensor module is affixed or within which the sensor module is embedded. Thus, after the recognition process, each time the one or more electronic devices receive the pressure wave from the sensor module, the electronic device can associate the pressure wave with the instrument.

The remote system 130 can include one or more computing devices operating as servers to manage data/information regarding a user's profile, account, performance, and/or any other data/information associated with the user. In exemplary embodiments, the electronic device(s) 120 can communicate with the remote system 130 to transmit and receive information using, e.g., electromagnetic radiation, such as radio frequency communications. As one example, the remote system 130 can be programmed and/or configured to receive user performance information from the electronic device(s) 120 and to process and/or analyze the performance information to determine statistics regarding the users performance and/or to provide an analysis regarding a user's mechanics (e.g., a swing analysis). Some statistics and swing analysis information that can be determined by the remote system 130 can include a swing tempo, swing velocity, swing force, club face angle, swing plane, and/or impact force with which the instrument strikes or will strike an object, and/or any other swing parameters as well as club consistency (e.g., variations in shot distances), putting stats (e.g., average putts per hole, 2-putt percentage, 3+ putt-percentage, 1 putt per round, etc.), scrambling statistics (e.g., the golfer's ability to get par when hitting the green in regulation is missed), sand saves (e.g., the ability of a golfer to get par when the ball lands in a bunker during a hole), fairway hits (e.g., percentage of times a golfer hits the fairway when the golf ball is hit from the tee), and the like.

Subsequent to determining the statistics and/or providing the analysis, the remote system 130 can transmit the statistics and/or analysis to the electronic devices 120, which can be programmed to display the statistics and/or analysis to the users. As another example, the remote system 130 can be programmed and/or configured to maintain golf course information, such as names of golf courses, geographic maps of golf courses including hole locations, a par for the holes of the golf courses, and/other suitable golf course information. The remote system 130 can transmit the golf course information to the electronic devices 120 upon request and/or can transmit the golf course information automatically. The golf course information can allow the electronic devices 120 to display the golf course information to the users, use the golf course information for automatically determining a user's performance on a golf course, and/or overlay the users performance on the golf course information rendered on a display.

In one exemplary embodiment, the system 100 can be implemented to monitor and/or track a user playing a round of golf. For example, the instruments 102 can be golf clubs associated with a user, each of the golf clubs can have a sensor module 110 affixed thereto or embedded therein, and the electronic device(s) 120 can be a mobile phone or any other suitable portable electronic device that can be carried by the user that is capable of detecting pressure waves propagating in the air. The electronic device can also be configured to determine its geographic location (e.g., using GPS). For example, each sensor module 110 can be affixed to or embedded in a proximal end of a golf club where the handle or grip is disposed. The user can interact with the user's electronic device 120 to set up the system 100 for use with the golf clubs. For example, the electronic device 120 can be programmed and/or configured to prompt the user to enter information about the golf clubs when it detects pressure waves propagating from the sensor modules 110. Upon completion of the set up process, the electronic device 120 associates each of the sensor modules 110 with the corresponding golf clubs to which the sensor modules 110 are affixed or within which the sensor modules 110 are embedded (e.g., based on a frequency of the pressure wave or based on unique identifiers included in the pressure wave), such that when the electronic device 120 detects a subsequent pressure wave propagating from one of the sensor modules 110, the electronic device 120 can be programmed to identify the golf club used by the user based on the detection of the pressure wave.

As the user plays a round of golf, the system 100 can monitor and/or track which golf clubs were used by the golfer for which holes and shots, a distance the golf ball traveled for each shot, geographic locations of the user, holes that have been completed by the user, holes that the user still has to complete, a golf score of the user, and/or other performance information associated with the round of golf being played by the user.

The electronic device 120 can store the performance information associated with the golf round and/or can render one or more GUIs that can be viewed by the user during and/or after the golf round. In some embodiments, the electronic device 120 can transmit the performance information to the remote system 130 for further processing and/or storage. The user may access the remote system 130 through the electronic device 120 and/or another electronic device (e.g., a laptop, desktop, or personal computer) to review, modify, update, delete, share, and the like, the performance information captured by the system 100.

Figure 2:
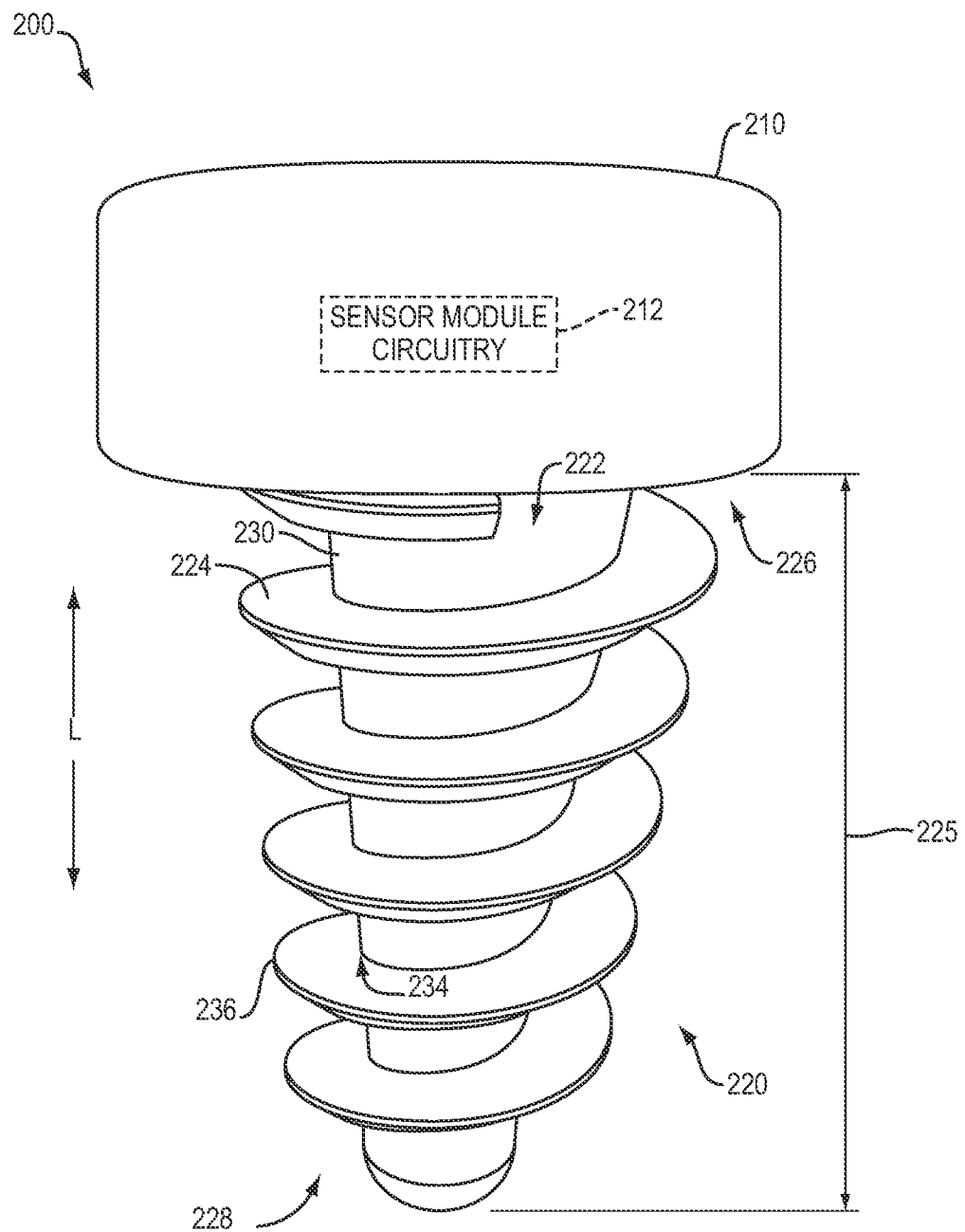
FIG. 2 is an exemplary embodiment of a sensor module that can be implemented in accordance with the present disclosure.

FIG. 2 is an exemplary embodiment of a sensor module 200 that can be affixed to an instrument in accordance with the present disclosure. For example, the sensor module 200 can be implemented as an embodiment of the sensor modules 110 depicted in FIG. 1. The sensor module 200 can include a housing portion 210 and a fastening portion 220. The housing portion 210 can house sensor module circuitry 212 that can be programmed and/or configured to perform one or more operations, tasks, functions, and/or processes described herein. In some embodiments, the sensor module circuitry 212 itself can form a sensor module. That is, in exemplary embodiments, the sensor module substantially of the sensor module circuitry 212 (e.g., devoid of the housing portion 210 and fastening portion 220) The fastening portion 220 can be configured to secure or affix the sensor module 200 to an instrument (e.g., instrument 102). For example, the fastening portion 220 can include a shaft 222 having an external thread 224 that can be used to threadingly engage an instrument.

As shown in FIG. 2, in exemplary embodiments of the fastening portion 220, the shaft 222 can extend along a longitudinal axis L from a first proximal end 226 to a second distal end 228 defining a length 225 of the fastening portion 220. The shaft 222 can have a generally conical configuration for which the outer surface 230 of the shaft 222 generally tapers inwardly along the longitudinal axis L from the first proximal end 226 to the second distal end 228.

The external thread 224 can be disposed circumferentially about the outer surface 230 of the shaft 222 along the longitudinal axis to form a helical or spiral ridge around the shaft 222. The external thread 224 can have a trapezoidal thread form (i.e., the thread 224 can have a trapezoidal cross-sectional shape), a triangular thread form (i.e., the thread 224 can have a triangular cross-sectional shape), and/or can take any other suitable form or shape. The thread 224 can generally extend radially outward from the outer surface 230 of the shaft 220 from a root 234 of the thread 224 to a crest 236 of the thread 224. While the fastening portion 220 has been illustrated as including thread 224, exemplary embodiments of the present disclosure can be implemented using other fastening structures in conjunction with the threads 224 or instead of the threads 224. For example, in some embodiments, the fastening portion 220 can include one or more barbs, hooks, spikes, or any other suitable structures that protrude from the outer surface 230 and are operable to generally secure the sensor module 200 to a swinging instrument (e.g., to the grip of a golf club).

Figure 3:
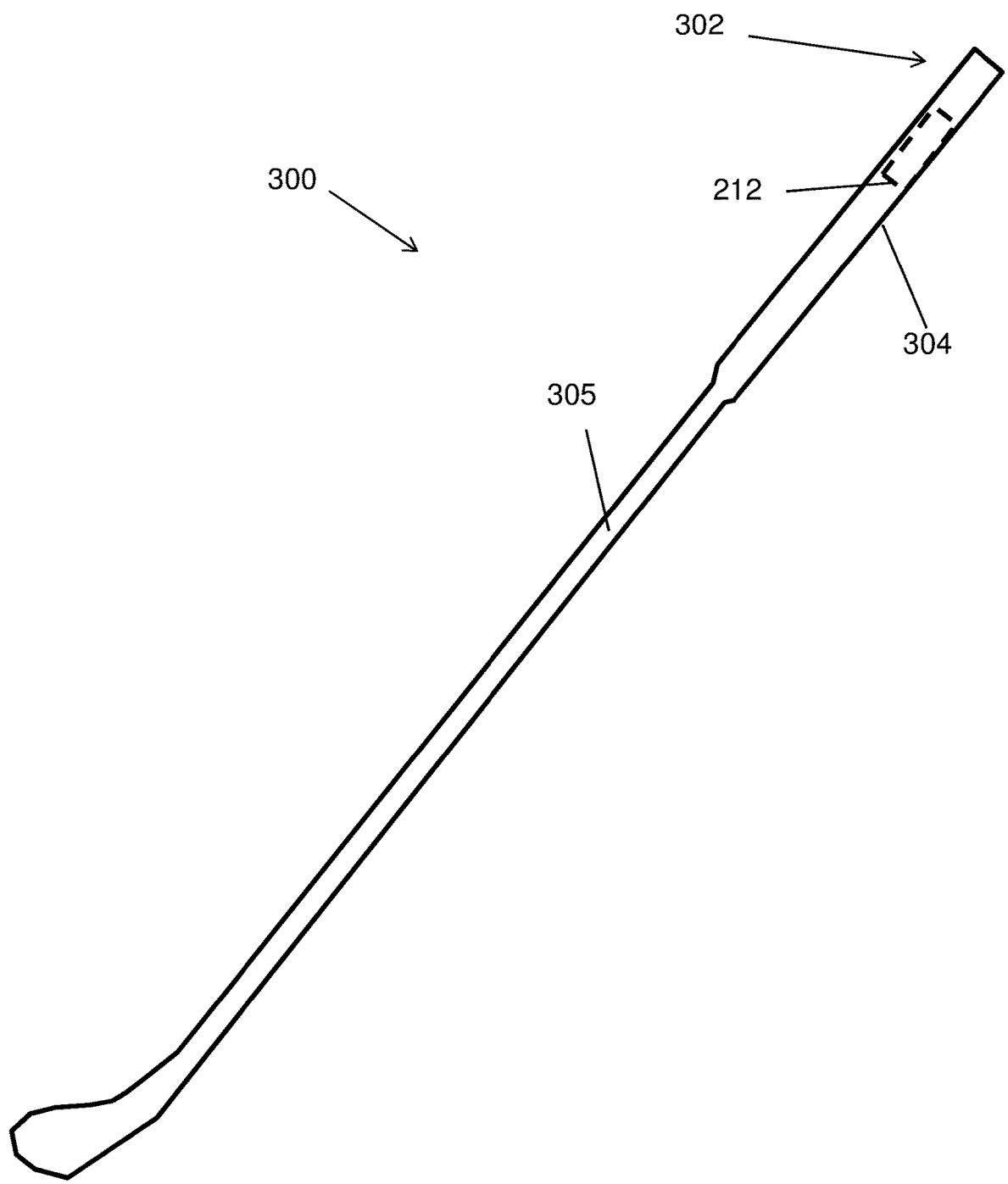
FIG. 3 is an exemplary embodiment of sensor module circuitry embedded in an instrument in accordance with the present disclosure.

FIG. 3 is an exemplary embodiment of sensor module circuitry 212 embedded in an instrument 300 in accordance with the present disclosure, where the sensor module circuit 212 forms a sensor module. In some embodiments, the sensor module circuitry 212 can be housed in a housing that is embedded within the instrument 300. As shown in FIG. 3, the sensor module circuitry 212 can be disposed within a shaft 305 the instruments 300. For example, the instrument 300 can be a golf club and the sensor module circuitry 212 can be disposed in the shaft of the club, for example, near a proximal end 302 of the golf club, where the handle or grip 304 is disposed.

Figure 4A:
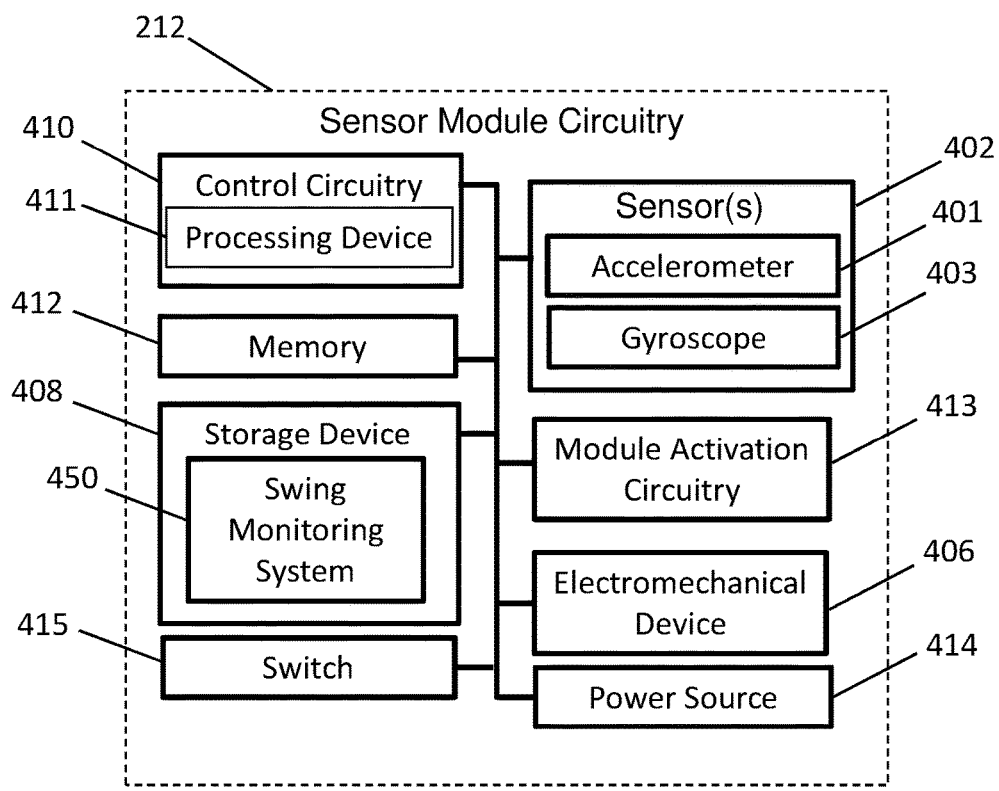
FIG. 4A is a block diagram of an exemplary embodiment of the sensor module circuitry that can be disposed with the sensor module shown in FIGS. 2 and 3.

FIG. 4A is a block diagram of an exemplary embodiment of the sensor module circuitry 212 that can be disposed within the sensor module 200 shown in FIG. 2 and/or embedded within the instrument 300 shown in FIG. 3. The sensor module circuitry 212 can include one or more sensors 402 (e.g., accelerometer 401, gyroscope 403, and/or any other suitable sensor), a electromechanical device 406, a storage device 408, control circuitry 410, memory 412 (e.g., RAM), a power source 414, and a switch 415.

The one or more sensors 402 can sense/detect one or more parameters associated with a use of the instruments, such as an acceleration, velocity, angular acceleration, orientation, position, impacts between the instruments and objects, and the like. The one or more sensors 402 can generate an output, e.g., including one or more sensor signals (e.g., electrical signals or otherwise), to the control circuitry 410. While the one or more sensors 402 are illustrated as including the accelerometer 401 and/or the gyroscope 403, the one or more sensors 402 can include more or fewer sensors. For example, in exemplary embodiments, the one or more sensors 402 can include any one of the accelerometer 401, gyroscope 403, and/or any suitable sensor, such as a magnetometer, pressure sensor, and/or capacitive sensor; any combination of sensors 402, such as any combination of the accelerometer 401, gyroscope 403, magnetometer, capacitive sensor, pressure sensor, etc.)

The multi-axis accelerometer 401 can include three or more axes of measurement and can output one or more signals corresponding to each axes of measurement and/or can output one or more signals corresponding to an aggregate or combination of the three axes of measurement. For example, in some embodiments, the accelerometer 401 can be a three-axis or three-dimensional accelerometer that includes three outputs (e.g., the accelerometer can output X, Y, and Z data). The accelerometer 401 can detect and monitor a magnitude and direction of acceleration, e.g., as a vector quantity, and/or can sense an orientation, vibration, and/or shock. For example, in exemplary embodiments, the accelerometer 401 can be used by the sensor module circuitry 212 determine an orientation and/or acceleration of an instrument to which the sensor module including the sensor module circuitry 212 is affixed. In some embodiments, the gyroscope 403 can be used instead or in addition to the accelerometer 401, to determine an orientation of an instrument to which the sensor module including the sensor module circuitry 212 is affixed and/or embedded. The orientation of the instrument can be used to determine when the user is preparing to swing the instrument and/or to identify and discriminate between different phases of a swing (e.g., back swing, forward swing). The acceleration can be used to determine when an impact occurs during a swing, a speed of the swing, a tempo of the swing, and/or any other motion parameters associated with swinging the instrument.

The acceleration and/or velocity can be used to identify and discriminate between different phases of a swing and determine whether an impact between the instrument and an object constitutes a shot. For example, during the backswing phase, a positive linear acceleration can be detected by the accelerometer. Approximately midway through the backswing, the velocity curve changes direction when the club slows down as it reaches the top of the backswing. When the curve changes direction, the acceleration is zero and linear velocity begins to decrease resulting in deceleration. At the end of the backswing phase, the club is temporarily static as the golf club changes direction, and therefore, no velocity is detected based on an output of the accelerometer 401. The downswing begins from the top of the backswing and as the club begins to move in a positive direction towards the ball, the linear acceleration increases. As the velocity approaches a constant value the rate of acceleration slowly begins to decrease and the downswing phase ends when an initial discontinuity in motion is detected by the accelerometer. This discontinuity marks the impact phase of the golf swing and the beginning of the follow through phase of the golf swing.

The electromechanical device 406 can be configured to generate pressure waves that propagate through air. The pressure waves can be formed by movement (e.g. vibrations) of the electromechanical device 406 in response to electrical control signals (e.g., received from the control circuitry 410). The pressure waves generated by the movement of the electromechanical device 406 can form alternating compressions and rarefactions in the air with a frequency (e.g., measured in hertz), amplitude/pressure (e.g., measured in decibels), and phase (e.g., measured in radian or degrees). In exemplary embodiments, the electromechanical device 406 can be a loud/audio speaker or a piezoelectric device. The pressure waves generated by the electromechanical device 406 can be sound waves. The pressure waves generated by the electromechanical device 406 can be detected by one or more electronic devices (e.g., electronic devices 120) to convey information to the electronic devices.

In some embodiments, the electromechanical device 406 can be configured and/or controlled to generate pressure waves that have a frequency that is above that which can be heard or perceived by some, most, or all humans (i.e. inaudible). As one example, in some embodiments, the electromechanical device 406 can generate pressure waves having a frequency of greater than approximately fifteen kilohertz or greater than approximately twenty kilohertz. As another example, in some embodiments, the electromechanical device can generate pressure waves having a frequency of approximately twenty kilohertz to approximately twenty-five kilohertz. As another example, the electromechanical device 406 can generate pressure waves having a frequency of approximately ten kilohertz to approximately sixty kilohertz. By generating pressure waves at a frequency that is above that which cannot be heard or perceived by some, most, or all humans (i.e. inaudible), exemplary embodiments of the present disclosure advantageously allow the sensor modules (i.e. via the electromechanical device) to communicate with a remote electronic device (i.e. via an electroacoustic transducer of the electronic device) without distracting a user before, during, and/or after swinging or otherwise using the instruments to which the sensor modules are affixed or embedded and/or or affecting a performance of the user before, during, and/or after swinging or otherwise using the instruments to which the sensor modules are affixed or embedded.

In some embodiments, the electromechanical device 406 can be configured and/or controlled to generate pressure waves that have a frequency that is within a frequency range that can be heard or perceived by some, most, or all humans (i.e. audible). For example, in some embodiments, the frequency of the pressure waves can be less than, e.g., approximately ten kilohertz, approximately fifteen kilohertz, or less than approximately twenty kilohertz. In some embodiments, to reduce and/or minimize distractions to a user, a pressure wave generated at a frequency that is audible to a user can be generated for a short duration of time (e.g., seconds or less), can be generated after the golf swing is completed, and/or can be generated to have an amplitude that results in a low decibel level to minimize and/or reduce distractions to a user.

In some embodiments, the electromechanical device 406 can be configured and/or controlled to generate pressure waves having audible or inaudible frequency that convey information that can be extracted by an electronic device that is separate, distinct, and spaced away from the sensor module. In some embodiments, the parameters of the pressure wave (e.g., amplitude, phase, frequency) can include the information that can be extracted by the electronic device. In some embodiments, the pressure wave can be modulated (e.g., using amplitude modulation, phase modulation, and/or frequency modulation) to encode information, which can be extracted by the electronic device. In some embodiments, the timing of the generation of the pressure waves can be controlled such that the pressure waves are generated after an impact between the golf club and an object is detected, after a golf swing is completed, and/or at any other suitable time. In some embodiments, the duration of the pressure wave (whether it has a frequency that is audible or inaudible) can be controlled. For example, in some embodiments, a pressure wave having a duration that is less than one second can be generated (e.g., a fraction of a second) and the pressure wave can include information that can be extracted by the electronic device, such as which sensor module generated the pressure wave, whether an impact between the golf club and an object was detected by the sensor module, swing analysis information, and/or any other suitable information. By generating a pressure wave that has a duration of a fraction of a second, the sensor module can reduce/minimize power consumption, and for embodiments that generate pressure waves having a frequency that is audible can minimize or reduce the likelihood that the pressure wave will distract a user.

The storage device 408 can include any suitable, non-transitory computer-readable storage medium, e.g., read-only memory (ROM), erasable programmable ROM (EPROM), electrically-erasable programmable ROM (EEPROM), flash memory, and the like. In exemplary embodiments, a swing monitoring system 450 can be embodied as computer-readable/executable program code stored on the non-transitory computer-readable storage device 408 and implemented using any suitable, high or low level computing language and/or platform, such as, e.g., Java, C, C++, C #, assembly code, machine readable language, and the like.

The memory 412 can include any suitable non-transitory computer-readable storage medium (e.g., random access memory (RAM), such as, e.g., static RAM (SRAM), dynamic RAM (DRAM), and the like). In some embodiments, the data/information and/or executable code for implementing the system 450 can be retrieved from the storage device 408 and copied to memory 412 during and/or upon implementation of the processes described herein. Once the data/information has be used, updated, modified, replaced, and the like, the data/information may be copied from memory 412 to the storage device 408.

The control circuitry 410 can include one or more logic-based devices, such as logic gates, flip-flops, field programmable logic arrays, timing generators, processing devices (e.g., microprocessors, digital signal processors, graphical processing units, microcontrollers), and/or any other suitable logic-based devices. In some embodiments, the processing device 411, memory 412, and possibly the storage 408, can be integrated in a single package or can be packaged separately and electrically coupled to each other through traces in a printed circuit board. In exemplary embodiments, at least a portion of the control circuitry 410 can be implemented as a processing device 411, which can include any suitable single- or multiple-core microprocessor of any suitable architecture that is capable of implementing and/or executing the system 450. The processing device 411 can be programmed and/or configured to execute the system 450 to implement one or more processes for monitoring and/or tracking usage of instruments by a user and to control the electromechanical device 406 to generate pressure waves corresponding to the usage of the instruments. The processing device 411 can retrieve information/data from, and store information/data to, the storage device 408 and/or memory 412. For example, user performance information, golf course information, performance statistics, user profiles, performance analysis, and/or any other suitable information/data for implemented the system 450 or that may be used by the system 450 may be stored on the storage device 408 and/or a memory 412. Some examples of performance information and/or performance analysis can include, for example, data output by the one or more sensors 402, an indication of a detected impact (e.g., a determined based on the data output by the one or more sensors 402), a golf shot (e.g., a determined based on the data output by the one or more sensors 402), a golf score, a swing tempo, swing velocity, swing force, club face angle, swing plane, and/or impact force with which the instrument strikes or will strike an object, and/or any other swing parameters as well as club consistency (e.g., variations in shot distances), putting stats (e.g., average putts per hole, 2-putt percentage, 3+ putt-percentage, 1 putt per round, etc.), scrambling statistics (e.g., the golfer's ability to get par when hitting the green in regulation is missed), sand saves (e.g., the ability of a golfer to get par when the ball lands in a bunker during a hole), fairway hits (e.g., percentage of times a golfer hits the fairway when the golf ball is hit from the tee), and the like.

In exemplary embodiments, the processing device 411 can be programmed to execute the system 450 to receive and process information/data from the one or more sensors 402, storage device 408, and/or memory 412; can be programmed to output control signals to the electromechanical device 406 to control the electromechanical device 406 to generate pressure waves to convey information/data to the electronic devices based on the execution of the system 450; and can be programmed to output data/information to the storage device 408 and/or the memory 412 based on the execution of the system 450. As one example, when the one or more sensors 402 includes the accelerometer 401, the processing device 411 can receive information/data output from the accelerometer corresponding to a direction force along one or more of the axes of the accelerometer 401, and can control the electromechanical device 406 to generate pressure waves to convey information/data associated with the output of the accelerometer 401, to an electronic device (e.g., the electronic device(s) 120). As another example, the processing device 411 can receive information/data output from the accelerometer 401 corresponding to a directional force along one or more of the axes of the accelerometer 401; can process the information/data to generate an indicator associated with an impact between the instrument to which the sensor module is secured and an object; and can control the electromechanical device 406 to generate a pressure wave in response to detection of the impact to indicate the impact to the electronic device.

In exemplary embodiments, the control circuitry 410 (e.g., via the processing device 411) can control the electromechanical device 406 to generate a continuous pressure wave that propagates through air at a frequency, amplitude, and phase. An electronic device can include a transducer for receiving pressure wave and converting the pressure wave to electrical signals. The electronic device can determine from which sensor the pressure wave propagates based on the frequency and can determine based on detection of the pressure wave that an impact between the instrument to which the sensor module is affixed or embedded was detected by the sensor module.

In exemplary embodiments, the control circuitry 410 (e.g., via the processing device 411) can control the electromechanical device 406 to generate a pressure wave having a modulate frequency, amplitude, or phase to encode information/data generated, derived, or output from the one or more sensors 402 as well as information/data associated with the sensor module. For example, the control circuitry 410 (e.g., via the processing device 411) can control the electromechanical device 406 to generate a pressure wave using frequency modulation, phase modulation, amplitude modulation, and/or a combination of frequency modulation, phase modulation, amplitude modulation. The modulated pressure wave can encode multi-symbol string (e.g., binary or greater) that can be extracted and interpreted by the electronic device. The information/data encoded in the modulated pressure wave can include an identification parameter that identifies which sensor module generated the pressure wave, an indication that the sensor module detected an impact between the instrument to which the sensor module is affixed or embedded, raw sensor data, swing information derived from raw sensor data, and/or any other suitable information/data. An electronic device can detect the modulated pressure wave via a transducer and can determine from which sensor module the pressure wave propagates by demodulating the modulated pressure wave (e.g., after the modulated pressure wave is converted to electrical signals by a transducer of the electronic device) and extracting the identification parameter included in the modulated pressure wave, and/or can extract any other information/data from the demodulated pressure wave. In some embodiments, the electronic device can determine that an impact occurred between the instrument to which the sensor module is affixed or embedded and an object based on detection of the modulated pressure wave from the sensor module (after associating the detected modulated pressure wave with the sensor module based on the identification parameter that is extracted from the modulated pressure wave. In some embodiments, the electronic device can determine that an impact occurred between the instrument to which the sensor module is affixed or embedded and an object by extracting an indication of the impact encoded in the modulated pressure wave. Thus, in some embodiments, information/data can be determined or derived based on the presence of the pressure wave itself (whether modulated or not); in some embodiments, information/data can be embedded in and extracted from the modulated pressure wave; and/or in some embodiments, some information/data can be embedded in the modulated pressure wave and some information/data can be determined or derived based on the presence of the modulate pressure itself. In some embodiments, the electronic device can determine that an impact occurred between the instrument to which the sensor module is affixed or embedded and an object by extracting an indication of the impact encoded in the modulated pressure wave.

In some embodiments, the control circuitry 410 can include module activation circuitry 413, which can receive one or more output signals (e.g., X, Y, Z data) from the accelerometer 401 (or gyroscope 403) as inputs to the module activation circuitry 413 and can process the signals to determine whether the instrument to which the sensor module is affixed is within a specified addressing range for a specified period of time. In exemplary embodiments, the module activity circuitry 413 can output one or more signals to the processing device 411 in response to the processing of the signals from the accelerometer 401 (or gyroscope 403). The processing device 411 can use the signals from the module activation circuitry to change a mode of operation of the sensor module circuitry (e.g., from a sleep mode of operation to a normal mode of operation or vice versa). While exemplary embodiments have been illustrated to include module activation circuitry, those skilled in the art will recognize that, in exemplary embodiments, the processing device 411 may be programmed and/or configured to process the output signals of the accelerometer 401 (or gyroscope 403) (e.g., without the module activation circuitry 413) to determine when to change the mode of operation of the sensor module circuitry.

Figure 4B:
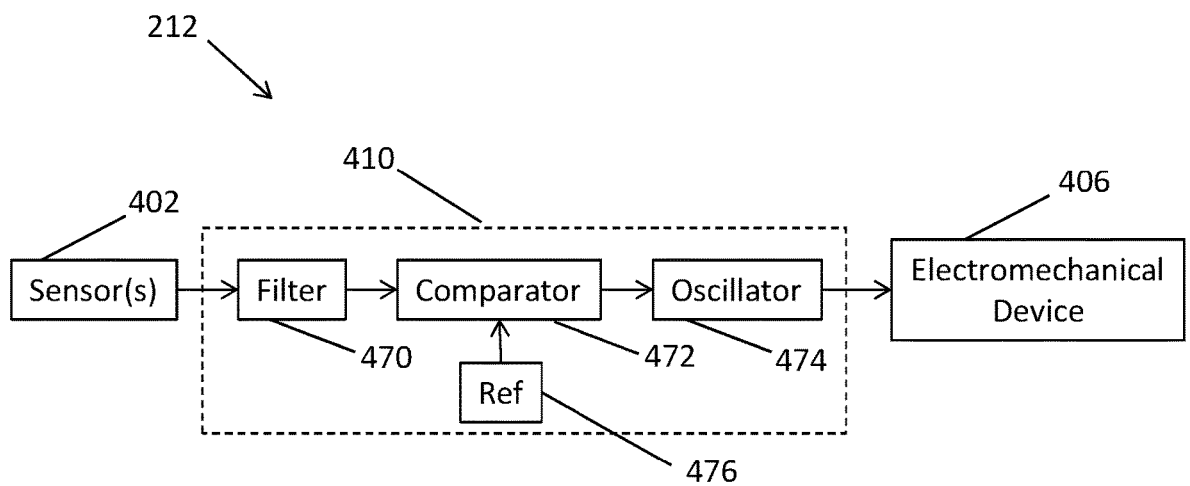
FIG. 4B is a block diagram of another exemplary embodiment of the sensor module circuitry that can be disposed with the sensor module shown in FIGS. 2 and 3.

While a non-limiting embodiment of the control circuitry has been illustrated as including a processing device, memory, and storage, exemplary embodiments of the control circuitry can be implemented without a processing device, memory, and/or storage. As one example, the control circuitry can include one or more logic-gates operatively coupled to each other to form a conditional logic circuit that outputs a control signal to the electromechanical device 406 in response to detection of one or more outputs from the one or more sensors 402. For example, during a golf swing the accelerometer can output a first peak acceleration associated with a back swing, which can cause a first condition of the conditional logic circuit to be satisfied; can output a second peak acceleration associated with a forward swing, which can cause a second condition of the conditional logic circuit to be satisfied; and can output a third peak acceleration associated with an impact, which can cause a third condition of the conditional logic circuit to be satisfied. In response to satisfaction of the first, second, and third conditions (e.g., in that sequence), the conditional logic circuit can output a control signal to the electromechanical device 406 to generate a pressure wave (modulated or not). As another example, as shown in FIG. 4B, the control circuitry 410 can include analog circuit elements, e.g., in the form of an amplified analog filter 470 that receives an output from the one or more sensors 402 followed by an analog comparator 472 driving an analog oscillator 474 to control the electromechanical device 406 to generate a pressure wave, e.g., when an impact is occurring or occurred. The comparator 472 can receive as, an input, an output of the filter and a reference generated by reference source 476. The output of the comparator 472 can activate the oscillator or selectively control a connection between the oscillator and the electromechanical device 406 (e.g., a switch) to control pressure wave generation by the electromechanical device 406.

The power source 414 can be implemented as a battery or capacitive elements configured to store an electric charge. As one example, in some embodiments, the power source can be a button cell lithium battery, such as a CR2032 battery, a CR2354 battery, or any other suitable power source. In some embodiments, the battery may be replaceable by the user. As another example, in some embodiments, the power source 414 can be a rechargeable power source, such as a battery or one or more capacitive elements configured to be recharged via a connection to an external power supply and/or to be recharged by an energy harvesting device. As one example, the rechargeable power source can be recharged using solar energy (e.g., by incorporating photovoltaic or solar cells on the housing on the sensor module), through physical movement (e.g., by incorporating a piezo-electric elements in the sensor module), and/or through any other suitable energy harvesting techniques using any suitable energy harvesting devices.

The switch 415 can be operatively coupled to the processing device 411 to trigger one or more operations by the processing device 410. In some embodiments, the switch 415 can be implemented as a momentary push button, rocker, and/or toggle switch that can be activated by a user. For example, in exemplary embodiments, the switch 415 can be activated by the user to instruct the processing device 411 to control the electromechanical device to generate a pressure wave during an association or initial recognition process to associate the sensor module with an electronic device.

Figure 5:
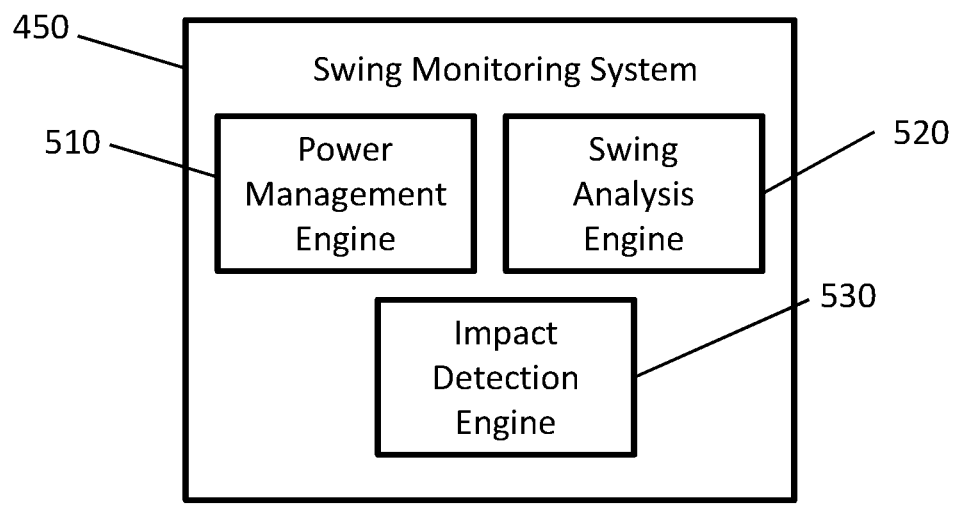
FIG. 5 is a block diagram of an exemplary embodiment of a swing monitoring system in accordance with the present disclosure.

FIG. 5 is a block diagram of an exemplary embodiment of the swing monitoring system 450 that can be executed by embodiments of the present disclosure that include a processing device 411 to facilitate monitoring and/or detecting swing events and/or impacts between an instrument and an object. The system 450 can include a power management engine 510, a swing analysis engine 520, and an impact detection engine 530.

The power management engine 510 can be programmed and/or configured to monitor and/or manage power consumption of the sensor module circuitry 212. For example, exemplary embodiments of the power management engine 510 can be configured control an operational state of the sensor module circuitry 212 so that the circuitry 212 can have different modes of operation, such as a sleep mode of operation and/or a normal mode of operation. The power management engine 510 can be programmed and/or configured to switch the operational state of the circuitry 212 between the different operation modes based on, for example, an orientation of the sensor module, acceleration of the sensor, impact between the instrument and an object, and/or a specified time period after an occurrence of one or more events, as determine by the circuitry 212 disposed within a sensor module.

In exemplary embodiments, the power management engine 510 can place the circuitry in the sleep mode of operation until the instrument to which the sensor module, including the circuitry 212, is affixed has a specified orientation, as detected by the accelerometer (and/or gyroscope). For example, for embodiments in which the sensor module is affixed to or embedded within a golf club, the sensor(s) 402 (e.g., the accelerometer 401 and/or gyroscope 403) can be configured to detect when the golf club is oriented in an initial swing position by a user (e.g., the addressing phase of a golf swing). The sensor(s) (e.g., the accelerometer 401 and/or gyroscope 403) can output a mode signal corresponding to the control circuitry when instrument has the specified orientation. In response to the mode signal from the sensor(s) (e.g., the accelerometer 401 and/or the gyroscope 403), the power management engine 510 can be executed by the control circuitry to transition the circuitry 212 from the sleep mode to the normal mode of operation, at which time the swing analysis engine 520 and impact detection engine 530 can be executed. In exemplary embodiments, the power management engine 510 can be executed by the processing device 411 to transition from the normal mode to the sleep mode based on, for example, an amount of time that elapsed since the circuitry 212 entered the normal mode of operation, an amount of time that elapsed after a completed swing has been detected, an amount of time that elapsed after the circuitry 212 generates pressure waves related to the swing event, and the like.

The swing analysis engine 520 can be programmed and/or configured to monitor a swing event associated with the instrument to which the sensor module is affixed, or within which the sensor module is embedded, and can be executed by the processing device 411 to capture and/or store information/data related to a swing of the instrument by a user upon detection by the circuitry 212 that the instrument has an initial swing orientation (e.g., the addressing phase of the golf swing). For example, the accelerometer 401 can output one or more signals (e.g., X, Y, Z data) to the processing device 411 as the instrument is being swung that correspond to a position, orientation, and acceleration of the instrument and the processing device can execute the swing analysis engine 520 to capture the position, orientation, acceleration, and direction of acceleration of the instrument during the swing event. The swing analysis engine 520 can be executed by the processing device to determine and/or discriminate between different phases of the swing (e.g., addressing, back swing, down swing, impact, and follow through), a swing tempo, swing velocity, swing force, club face angle, swing plane, and/or impact force with which the instrument strikes or will strike an object, and/or any other swing parameters.

The impact detection engine 530 can be programmed and/or configured to monitor and/or determine when the instrument strikes an object, e.g., during a swing event. In exemplary embodiments, the impact detection engine 530 can be executed by the processing device 411 to specify a valid window of a swing event over which an impact can be detected and/or can process one or more signals output by the accelerometer 401 and received by the processing device. For example, in some embodiments, the impact detection engine 530 can be programmed and/or configured to detect impacts between the instrument and an object during the downswing phase, the impact phase, and/or the follow-through phase of a golf swing. If an impact detection does not occur within the window defined by the impact detection engine 530, the impact detection engine 530 can ignore the impact.

In some embodiments, the impact detection engine 530 can be programmed and/or configured to determine when an impact occurs based on an output from the sensor(s) 402 (e.g., the accelerometer 401). In some embodiments, the engine 530 can analyze a movement (e.g. acceleration) of the instrument for a predetermined time before the impact and a predetermined time after the impact. Based on this analysis, in some embodiments, the impact detection engine 530 can determine whether a golf shot occurred or whether there was a false detection. For example, the acceleration characteristics of the downswing phase and follow-through phase immediately before and immediately after impact, respectively, can be defined and the impact detection engine 530 can be executed by the processing device 411 to determine whether the measured accelerations during the predetermined time periods correspond to the acceleration characteristics of a golf swing.

In exemplary embodiments of the present disclosure, the impact detection engine 530 can be programmed and/or configured to suppress or ignore detection of false positive golf shots based on one or more criteria. The criteria can be used in aggregate and/or combination to detect false positive different circumstances or events to provide for robust and accurate detection of golf shots.

In some embodiments, the impact detection engine 530 can be executed by the processing device to suppress detection of a false positive golf shot when, for example, a golf club is dropped (e.g., into a golf bag) by analyzing the x, y and z accelerometer output values before a detected impact (e.g., motion criteria). If the x, y, z accelerometer values are sufficiently small, the impact detection engine 530 can be programmed to assume that the club was dropped (e.g., into a bag). If the "wakeup" or "sleep" states are triggered (which can mean that the golf club was turned upright after the shot, the false positive suppression can be canceled and the shot can be recognized. This approach advantageously allows for the recognition of very small swings (e.g. such as chip shots).

In some embodiments, detection of a false positive golf shot can be detected by the impact detection engine 530 based on motion by sampling and/or analyzing the accelerometer data for a predetermined time period after the impact (e.g., time criteria). For example, in some embodiments, the seconds between approximately the 3rd second after impact and the 11th second after impact can be sampled and analyzed. If the values output by the accelerometer are sufficiently small, the impact detection engine 530 can be programmed to determine, for example, that the club was thrown on the ground and the detected impact can be suppressed or ignored.

In some embodiments, a false positive can be suppressed or ignored based on a time between detected impacts (e.g., time criteria). As an example, the time criteria can be a time period that begins when a first impact is detected. In some embodiments, one of the detected impacts can be counted as the golf shot and the other detected impacts can during the time period can be ignored. As another example, the time criteria can be a frequency are rate between consecutive detected impacts such that if impacts occur at a frequency or rate that exceeds a threshold frequency or rate, all but one of the impacts can be counted and the other impacts can be ignored.

For embodiments in which the impact detection engine 530 suppresses or ignores false positive golf shots, the processing device 410 of the sensor module circuitry 212 can execute the impact detection engine 530 to indicate detection of a golf shot. For example, in some embodiments, the processing device can be programmed and/or configured to control the electromechanical device to generate pressure waves indicating that a golf shot occurred. In some embodiments, the processing device can be programmed and/or configured to control the electromechanical device to generate pressure waves including the accelerometer data and/or other swing information. In some embodiments, when the electronic device detects a pressure wave including acceleration data and/or swing information, the electronic device can be programmed to automatically associate the received data/information included in the pressure waves with a golf shot such that the pressure waves propagating from the circuitry 212 does not require a specific indicator that a golf shot was detected. In the event that an impact processed by the impact detection engine 530 is determined to be a false positive, in some embodiments, the processing device can execute the engine 530 to delete, ignore, or otherwise disregard the impact such that no pressure waves are generated. In some embodiments, the circuitry 212 can be programmed to generate pressure waves including the acceleration information and an indication that the detected impact was a false positive so that the electronic device can process or ignore the received data/information based on the indication.

While an exemplary embodiment of the system 450 has been illustrated with the power management engine 510, the swing analysis engine 520, and the impact detection engine 530, those skilled in the art will recognize that engines 510, 520, and/or 530 can be integrated with each other to form a single engine. Furthermore, while an exemplary embodiment of the system 450 includes the engines 510, 520, and 530, those skilled in the art will recognize that each of the engines 510, 520, and 530 can be implemented as several different engines such that the operation of the each of the engines 510, 520, and 530 can be performed by a combination of engines.

While the engines 510, 520, and 530 are illustrated as being resident in the sensor module, exemplary embodiments of the present are not limited to this configuration. For example, in exemplary embodiments, the operation, functionality, and/or processes of the engines 510, 520, and/or 530 can be resident on and/or implemented by the electronic device.

Figure 6:
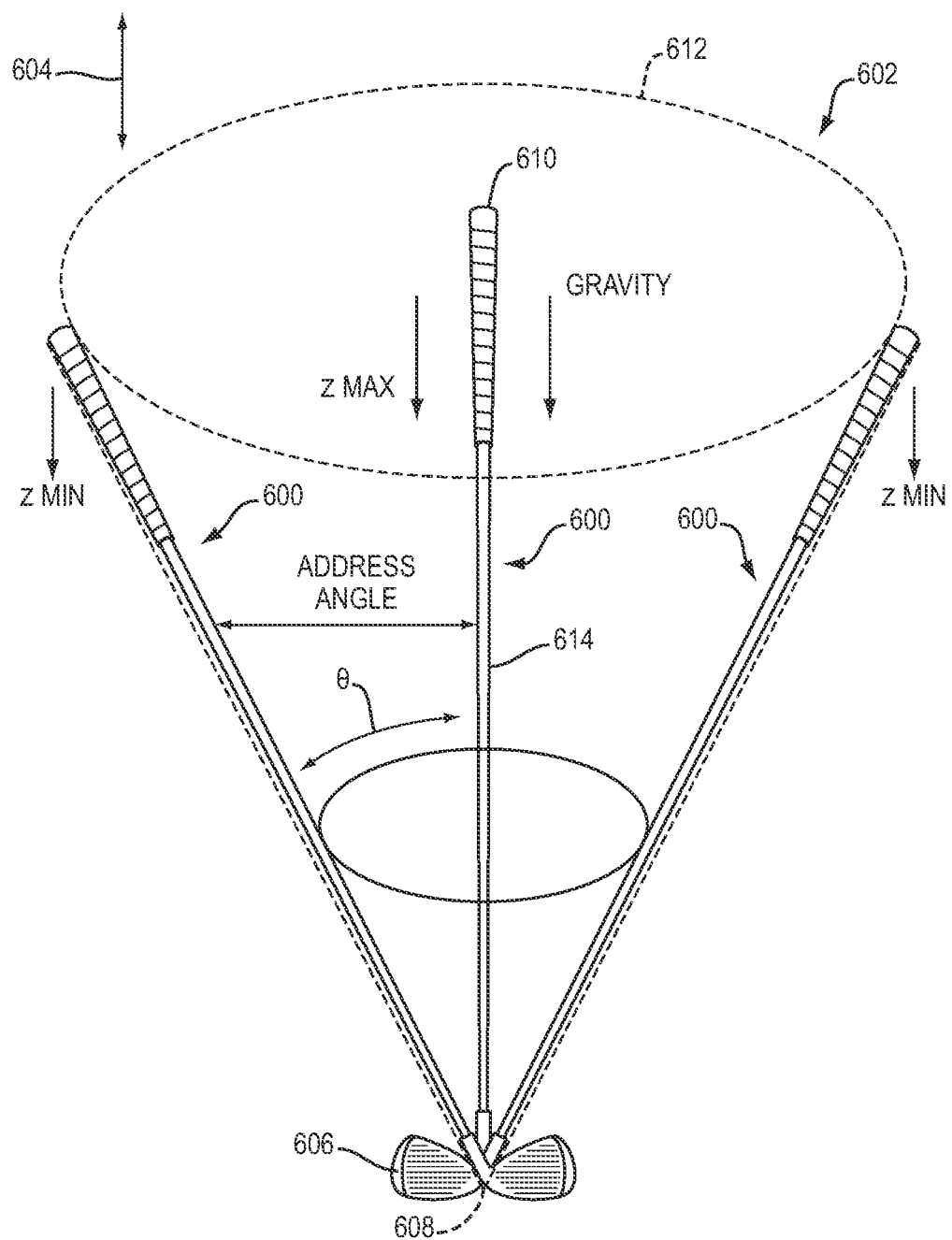
FIG. 6 depicts an exemplary range of orientations of a swinging instrument that facilitate a change in the operational mode of the sensor module circuitry in accordance with exemplary embodiments of the present disclosure.

FIG. 6 depicts an exemplary range of orientations of a golf club 600 (e.g., an embodiment of the instruments 102) that can be identified by embodiments of the circuitry 212 as an initial swing position of the golf club 600 (e.g., the addressing phase of a golf swing) and can be utilized by the circuitry to transition from the sleep mode of operation to the normal mode of operation. To reduce overall power consumption and/or extend the useable life of a nonrenewable power source that can be utilized by the circuitry 212, the range of orientations can be defined to ensure that the circuitry 212 operates in the normal mode of operations for as little time as possible by making the transition from the sleep mode to the normal conditional upon detection of the orientation of the instrument within the defined range of orientations. In the present embodiment, the range of orientations of the golf club 600 can be an acceptance cone 602 such that when the golf club has an orientation that is within the acceptance cone 602, the golf club satisfies a condition for transitioning between the sleep mode of operation and the normal mode of operation.

As described herein, the accelerometer (and/or gyroscope) of embodiments of the circuitry 212 can include three or more axes of measurement and can output one or more signals corresponding to each axes of measurement and/or can output one or more signals corresponding to an aggregate of combination of the three axes of measurement. The acceptance cone 602 can be defined by specifying a minimum directional force (z min) (e.g., having a magnitude and a direction) sensed by the accelerometer (due to gravity) along a z-axis 604 (i.e. the vertical axis) when the head 606 of the golf club 600 is oriented downwardly at an apex 608 of the acceptance cone 602 and a grip 610 of the golf club 600 is oriented above the head and at a base 612 of the acceptance cone. A maximum directional force along the z-axis (z max) can be measured when a shaft 614 of the golf club 600 is parallel to the z-axis (e.g., perpendicular to an x-axis and a y-axis). The minimum direction force (z min) can correspond to an angle θ of the golf club relative to the z-axis 604. In exemplary embodiments, the angle θ can be referred to as an addressing angle and can be approximately 25 degrees to approximately 80 degrees relative to the z-axis 604 (e.g., measured from perpendicular to the ground).

When the orientation of the head 606 and the grip 610 are inversed such that the grip is disposed downwardly at the apex of the acceptance cone 602 and the head 606 is disposed above the grip 610 and at the base 612, the directional force along the z-axis 604 can have an identical magnitude, but a different directional component as the original orientation. Embodiments of the circuitry 212 can be configured such that this inverse orientation does not satisfy the conditions of the acceptance cone 602. In exemplary embodiments, the parameters of the acceptance cone 602 (e.g., minimum directional force along the z-axis) can be implemented using software (e.g., the battery management engine 410) and/or hardware components (e.g., the activation circuitry 413).

Figure 7:
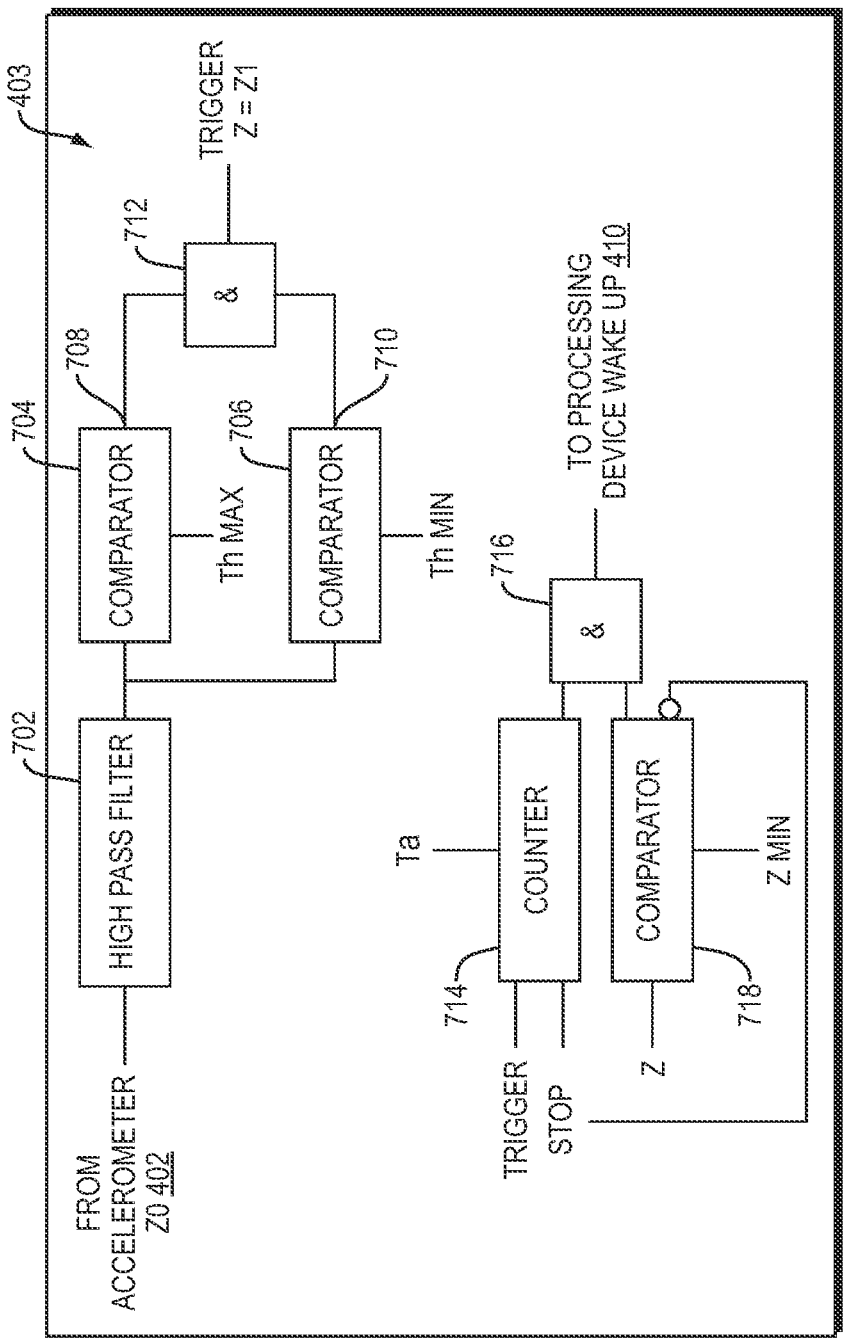
FIG. 7 is a block diagram of an exemplary hardware implementation of module activation circuitry in accordance with exemplary embodiments of the present disclosure.

FIG. 7 is a block diagram of an exemplary hardware implementation of the module activation circuitry 413 in accordance with exemplary embodiments of the present disclosure. As described herein, the sensor module can remain in a sleep mode until the sensor module detects that an instrument to which the sensor module is attached is oriented within an acceptance cone. The circuitry 413 can be used by the sensor module to determine whether the instrument is within the acceptance cone and can output a signal to the processing device of the sensor module circuitry, which can be programmed and/or configured to transition from a sleep mode of operation to a normal mode of operation.

As shown in FIG. 7, the activation circuitry 413 can receive an output signal $Z_O$ from the accelerometer 402 corresponding to a sensed force along the z-axis of the accelerometer included in the sensor module circuitry. The output signal $Z_O$ can be passed through a high pass filter 702, and can subsequently be received as an input by comparators 704 and 706. The comparator 704 can compare the filtered output signal to a maximum threshold value (Th max) and the comparator 706 can compare the output signal $Z_O$ to a minimum threshold value (Th min). The outputs 708 and 710 of the comparators 704 and 706, respectively, can be input to an AND gate 712. If the outputs 708 and 710 of the comparators 704 and 706, respectively, are both a Boolean one (e.g., if the outputs 708 and 710 have voltage above a specified threshold voltage), the AND gate 712 can output a trigger. Otherwise, the AND gate 712 does not output a trigger.

When the trigger is output by the AND gate 712 it is received as an input by a counter 714 to initiate and start the counter 714. The counter 714 can be programmed and/or configured to increment a counter value until the counter value reaches a threshold counter value $T_a$ and/or until the counter receives a stop signal. If the counter 714 reaches the threshold counter value $T_a$, the counter 714 outputs a Boolean one (e.g., the output from the counter 714 has voltage above a specified threshold voltage). Otherwise, the counter 714 outputs a Boolean zero (e.g., the output from the counter 714 has voltage below a specified threshold voltage). The output of the counter 714 is received as a first input to an AND gate 716 and an output of a comparator 718 is received by the AND gate 716 is a second input.

The comparator 718 compares the output of the accelerometer associated with the sensed force along the z-axis with the specified minimum directional force (z min) to determine whether the instrument (e.g., golf club) remains within the acceptance cone for the duration of the time period defined by the threshold counter value $T_a$. When the sensed force along the z-axis is greater than the specified minimum directional force (z min), the comparator 718 outputs a Boolean one to the AND gate 716 and outputs a Boolean zero to an input of the counter 714 corresponding to a control input for stopping the counter 714. When the sensed force along the z-axis is greater than the specified minimum directional force (z min), the comparator 718 outputs a Boolean one to the AND gate 716 and outputs a Boolean zero to an input of the counter 714 corresponding to a control input for stopping the counter 714. A Boolean one output from the comparator 718 to the control input of the counter 714 stops the counter from incrementing the counter value, and in some embodiments, can reset the counter value to an initial value (e.g., zero). The counter 714 may not restart until the counter 714 receives another trigger signal and the control input of the counter 714 is a Boolean zero. The AND gate 716 can output a wake signal to the processing device of the sensor module circuitry in response to simultaneously receiving a Boolean one from the output of the counter and a Boolean one from the output of the comparator. The processing device can execute the power management engine to transition the mode of operation of the sensor module circuitry from the sleep mode to the normal mode of operation. After the sensor module circuitry transitions to the normal mode of operation, the processing device executing the power management engine can determine whether the instrument (e.g., a golf club) is swung within a specified time period. If not, the processing device executing the power management engine can transition the sensor module circuitry from the normal mode of operation to the sleep mode of operation.

Figure 8:
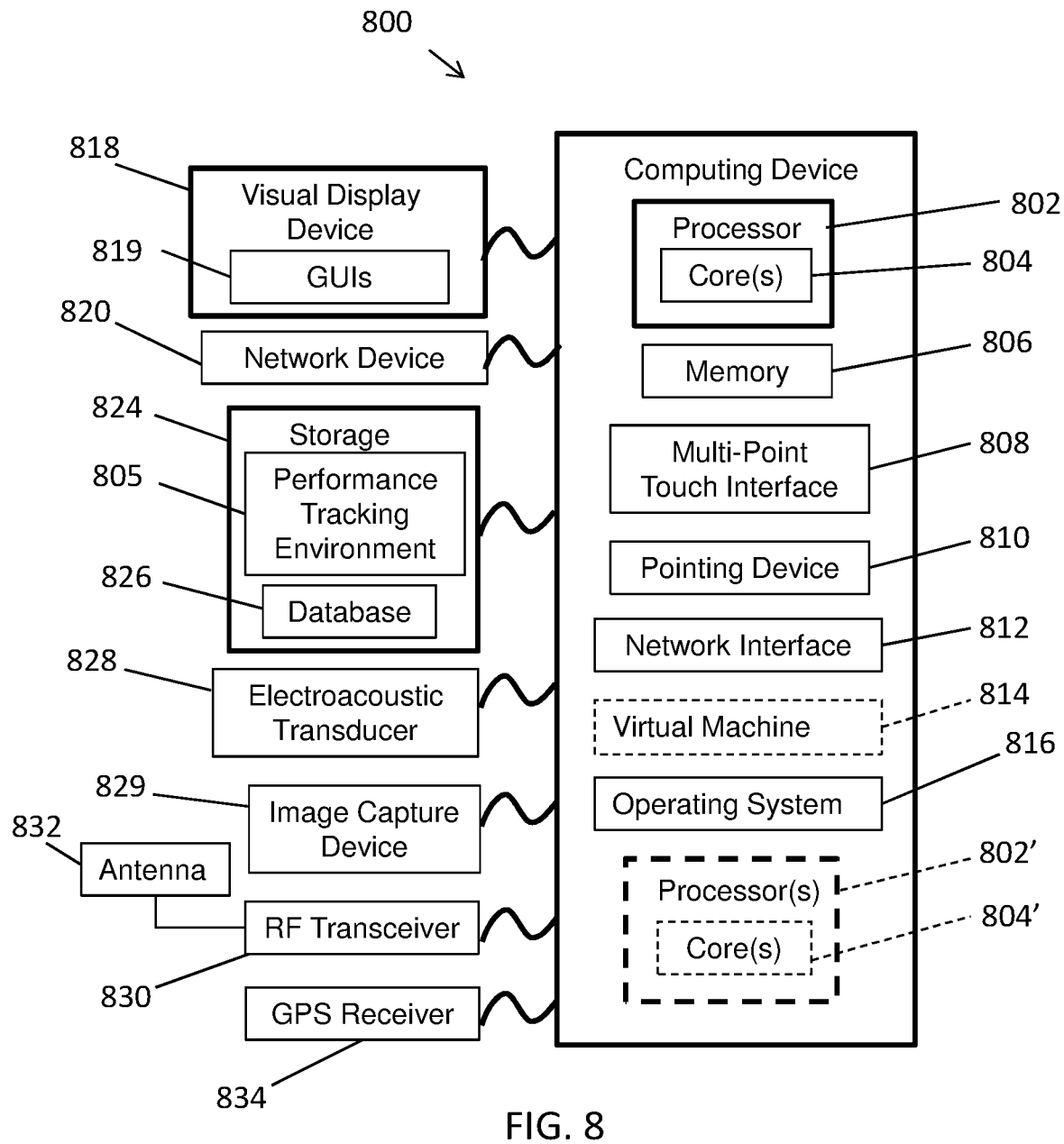
FIG. 8 is a block diagram of an electronic device that can be implemented in the performance monitoring system in accordance with exemplary embodiments of the present disclosure.

FIG. 8 is a block diagram of an exemplary electronic device 800 that may be used to implement exemplary embodiments of the electronic device 120 described herein. The electronic device 800 can include a computing device that includes one or more non-transitory computer-readable media for storing computer-executable instructions, code, or software for implementing a performance tracking and/or monitoring environment 805. The non-transitory computer-readable media may include, but are not limited to, one or more types of hardware memory, non-transitory tangible media (for example, one or more magnetic storage disks, one or more optical disks, one or more flash drives), and the like. For example, memory 806 included in the electronic device 800 may store computer-readable and computer-executable instructions or software for implementing exemplary embodiments of the environment 805. The computing device 800 also includes control circuitry in the form of configurable and/or programmable processing device(s), e.g., a processor 802 and associated core 804, and optionally, one or more additional configurable and/or programmable processor(s) 802' and associated core(s) 804' (for example, in the case of computer systems having multiple processors/cores), for executing computer-readable and computer-executable instructions or software stored in the memory 806 and other programs for controlling system hardware. Processor 802 and processor(s) 802' may each be a single core processor or multiple core (804 and 804') processor.

Virtualization may be employed in the electronic device 800 so that infrastructure and resources in the electronic device 800 may be shared dynamically. A virtual machine 814 may be provided to handle a process running on multiple processors so that the process appears to be using only one computing resource rather than multiple computing resources. Multiple virtual machines may also be used with one processor.

Memory 806 may include a computer system memory or random access memory, such as DRAM, SRAM, EDO RAM, and the like. Memory 806 may include other types of memory as well, or combinations thereof.

A user may interact with the electronic device 800 through a visual display device 818, such as a touch screen, which may display one or more graphical user interfaces 819 render upon execution of the computer readable instructions, code, or software corresponding to the environment 805. The electronic device 800 may include other I/O devices for receiving input from a user, for example, a keyboard (virtual or physical) or any suitable multi-point touch interface 808, a pointing device 810 (e.g., a mouse or stylus), an electroacoustic transducer 828 (such as a microphone, piezo-electric sensor) that converts mechanical energy of detected pressure waves into electrical signals, and/or an image capturing device 829 (e.g., a camera or scanner). The computing device 800 may include other suitable conventional I/O peripherals.

The electronic device 800 may also include one or more storage devices 824, such as a hard-drive, CD-ROM, or other computer readable media, for storing data and computer-readable instructions and/or software that implement exemplary embodiments of the environment 805 described herein. Exemplary storage device 824 may also store one or more databases for storing any suitable information required to implement exemplary embodiments. For example, exemplary storage device 824 can store one or more databases 826 for storing information, such as user performance information, golf course information, performance statistics, user profiles, performance analysis, and/or any other information to be used by embodiments of the environment 805. The databases may be updated manually or automatically at any suitable time to add, delete, and/or update one or more items in the databases.

The electronic device 800 can include a network interface 812 configured to interface via one or more network devices 820 with one or more networks, for example, Local Area Network (LAN), Wide Area Network (WAN) or the Internet through a variety of connections including, but not limited to, standard telephone lines, LAN or WAN links (for example, 802.11, T1, T3, 56 kb, X.25), broadband connections (for example, ISDN, Frame Relay, ATM), wireless connections, controller area network (CAN), or some combination of any or all of the above. The network interface 812 may include a built-in network adapter, network interface card, PCMCIA network card, card bus network adapter, wireless network adapter, USB network adapter, modem or any other device suitable for interfacing the electronic device 800 to any type of network capable of communication and performing the operations described herein.

In exemplary embodiments, the electronic device 800 can include a RF transceiver 830. The RF transceiver 830 can be configured to transmit and/or receive wireless transmissions via an antenna 832. For example, the RF transceiver can be configured to transmit one or more messages, directly or indirectly, to a remote system (e.g., remote system 130 shown in FIG. 1) and/or can be configured to receive one or more messages, directly or indirectly, from the remote system. The RF transceiver 830 can be configured to transmit and/or receive messages having a specified frequency and/or according to a specified sequence and/or packet arrangement. As one example, the RF transceiver 830 can be a WiFi transceiver configured to conform to a WiFi standard (e.g., as defined IEEE 802.11 standards) for transmitting and/or receiving radio transmissions typically in the frequency range of approximately 2.4 gigahertz (GHz) to approximately 2.48 GHz and/or can be a cellular transceiver configured to conform to one or more cellular protocols (e.g., GSM, LTE, 3G, 4G).

The electronic device can include a GPS receiver 834. The GPS receiver 834 can be configured to receive GPS satellite transmissions including GPS data, which can be used by the environment 805 being executed by the processor 802 of the electronic device 800 to monitor and/or track a geographic location of the electronic device 800 (e.g., a longitude and latitude of the electronic device). For example, for embodiments implemented in a golfing environment, the electronic device 800 can receive a broadcast signal from a GPS satellite and can process the GPS data included in broadcast signal to determine a geographic location of the electronic device 800, which can be utilized by the environment 805 to determine a geographic location of the electronic device 800 on a golf course, relative to a hole on the golf course, a distance the electronic device 800 traveled between consecutive golf shots, and/or any other location based information.

In some embodiments, the electronic device 800 may be any computer system, such as a laptop, handheld computer, tablet computer (e.g., the iPad™ tablet computer), mobile computing or communication device (e.g., the iPhone™ communication device or an Android™ communication device), or other form of computing or telecommunications device that is capable of communication and that has sufficient processor power and memory capacity to perform the operations described herein. In some embodiments, the electronic device 800 can be a device specifically created to monitor and/or track a golf round using the sensor modules. The electronic device 800 may run any operating system 816, such as any of the versions of the Microsoft® Windows® operating systems, the different releases of the Unix and Linux operating systems, any version of the MacOS® for Macintosh computers, any version of the Android™ operating system, any version of the iOS operating system for the Apple iPhone and/or iPAd, any embedded operating system, any real-time operating system, any open source operating system, any proprietary operating system, or any other operating system capable of running on the computing device and performing the operations described herein. In exemplary embodiments, the operating system 816 may be run in native mode or emulated mode. In an exemplary embodiment, the operating system 816 may be run on one or more cloud machine instances.

In exemplary embodiments, the processor 802 can "listen" for detection of pressure waves from the sensor modules based on an output of the electroacoustic transducer 828. For example, when the environment 805 is being executed in the foreground or background, the processor 802 can monitor an input corresponding to an output of the transducer 828 to determine whether the transducer 828 detected a pressure wave propagating from one or more of the sensor modules (e.g., based on movement or vibrations of the transducer in response to the pressure wave). In response to receipt of electrical signals corresponding to the pressure wave at the input of the processor 802 from the transducer 828, the processor 802 can process the electrical signals to determine information/data based on the receipt of the pressure wave itself and/or based on information/data encode in and extracted from the pressure wave. For example, in some embodiments, the electronic device 800 can detect pressure waves propagating from a sensor module that include acceleration information, other swing information, sensor module identification information, an indication that the sensor module detected an impact between the instrument and an object, and/or an indication of a golf shot.

In exemplary embodiments, in response to the receipt of the information/data included in the pressure waves, the processing device 802 of the electronic device 800 can execute the environment 805 to determine whether the impact associated with the detected pressure wave is a false positive golf shot. If the electronic device 800 determines that the impact is a false positive golf shot, the environment 805 can be executed by the processing device 802 to suppress or ignore the data/information included in the pressure wave or can be programmed to process the data/information included in the pressure wave as a false positive.

In exemplary embodiments, the environment 805 can be programmed and/or configured to suppress or ignore false positive golf shots based on one or more criteria. The criteria can be used in aggregate and/or combination to detect false positive different circumstances or events to provide for robust and accurate detection of golf shots. In some embodiments, the criteria can be used in conjunction with any criteria implemented by the sensor modules. For example, for embodiments in which the sensor modules are configured to process the accelerometer output to identify golf shots, if the sensor module determines that a detected impact constitutes a golf shot based on criteria used by the sensor module and creates a pressure wave indicative of a detected golf shot, the electronic device executing the environment 805 can apply its criteria to determine whether the detected impact is a golf shot or is a false positive upon detection of the pressure wave. In some embodiments, the electronic device 800 can receive acceleration information from the sensor module and can determine whether the acceleration information corresponds to a golf shot or a false positive.

In some embodiments, the environment 805 can be programmed and/or configured to suppress or ignore false positives when a club is dropped (e.g., into a bag) by processing x, y and z accelerometer output values (e.g., accelerometer criteria) obtained before, after, and/or when the impact is detected, which can be extracted from a pressure wave detected by the electronic device and generated by a sensor module. If the x, y and z accelerometer output values are sufficiently small, the processing device 802 can execute the environment 805 to assume that the club was dropped (e.g., into a bag) and to identify the impact as a false positive. If a "wakeup" or "sleep" state is triggered in the sensor module subsequent to impact (which means that the club was turned upright after the shot), the sensor module can include this information in a pressure wave and the electronic device 800 can cancel the false positive suppression and recognize the detected impact as a shot in response to detection and processing of the pressure wave. This advantageously allows the environment 805 executed in the electronic device to recognize very small swings (e.g., such as chip shots).

In some embodiments, a false positive golf shot can be suppressed or ignored based on a motion of the golf club before, during, or after an impact is detected. For example, after a shot, the accelerometer output values are sampled and processed for a predetermined amount of time and included in a pressure wave to be detected by the electronic device. In some embodiments, the seconds between approximately the third second after impact and the eleventh second after impact, can be processed and analyzed. If the values in the accelerometer are sufficiently small, the environment 805 can be programmed and/or configured to assume, for example, that the club was thrown on the ground and can suppress or processor 802 can execute the environment 805 to ignore the detected impact.

In some embodiments, a false positive impact/golf shot can be suppressed or ignored based on distances between detected impacts. For example, the environment 805 can be programmed and/or configured to recognize only one detected impact within a certain geographic radius (e.g., to form a geographic boundary) as a golf shot and can ignore other detected pressure waves associated with acceleration information or impacts within the geographic radius. The geographic radius can be different for different golf clubs and/or for different distances to a specified location on the golf course, such as a center point of the green of the current hole being played by the user. As one example, the geographic radius associated with a driver can be larger than the geographic radius associated with a long iron, which can be larger than the geographic radius of a short iron. The geographic radius can be defined based on GPS coordinates (e.g., longitude and latitude coordinates) and the distance can be measured using global positioning information processed by the electronic device 800 such that if multiple impacts are detected within the geographic radius only one of the detected impacts is counted as a golf shot. In some embodiments, the first, intermediate, or last detected impact can be counted as the golf shot and the first detected impact can define a point within the geographic radius (e.g., a center point). The geographic radius criteria can be used to advantageously eliminate false positives from practice shots (as well as from banging a golf club on the ground after a shot in frustration or any other impacts detected within the radius).

As a non-limiting example, during a round of golf, the user can begin a new golf hole such that no golf shots have been recorded for the golf hole. Before striking the golf ball, the user may take a series of practice swings near the tee site with the driver. In some embodiments, information related to these practice swings can be included in pressure waves output by the sensor module at the time the practice swings occur and the electronic device can maintain a running log of the swings upon detection of the pressure waves. In some embodiments, only those practice swings for which the sensor module secured to and/or embedded within the driver detects an impact are used to generate pressure waves to be detected by the electronic device. The propagation of a pressure wave in response to a first swing (or the first detected impact) can be used by the electronic device to establish a geographic boundary based on the type of club used to generated the pressure wave and/or a distance of the electronic device to the a specified location on the golf course (e.g., a distance to the center of the green for the current golf hole being played) determined based on golf course information and GPS data. For example, the location at which the electronic device detects a pressure wave from a sensor module for the first can be set to a center point of the geographic boundary and a geographic radius can be set to a specified geographic radius associated with the driver when the distance between the center point of the geographic boundary and the center of the green exceeds a threshold value.

Once the golfer is ready take an actual golf shot, the user can strike the ball with the driver and can move to the location at which the golf landed after being struck by the driver (i.e., the new location). The user can select one or more clubs at the new location and can take a series of practice swings and/or can strike the golf ball with the golf club, each of which can generate pressures waves from the sensor modules corresponding to the golf clubs used by the user, which can be detected by the electronic device. If the new location of the electronic device exceeds the geographic radius set by the electronic device when the pressure waves are detected, the electronic device identifies that a golf shot previously occurred based on one of the swings of the driver within the geographic radius.

In some embodiments, the location of the electronic device can be updated as the electronic device moves such that the electronic device can detect when the electronic device moves from within the geographic boundary to outside of the geographic boundary (e.g., when the electronic device breaks passes through a perimeter of the geographic boundary from an area within the boundary to an area outside of the boundary). Upon detecting that the electronic device is outside of the geographic boundary, the electronic device can automatically identify one of the swings/detected impacts that occurred in the geographic boundary as a golf shot and can wait for the next detection of a pressure wave to set a new geographic boundary (e.g., a new center point and geographic boundary) for the next golf shot.

In some embodiments, the electronic device can wait until the electronic device detects a pressure wave from one of the sensor modules while the electronic device is outside of the geographic boundary before assigning one of the swings/detected impacts as a golf shot that occurred within the geographic boundary and resetting the center point and geographic radius of the boundary based on the location at which the electronic device receives the next pressure wave from the sensor module outside the previously established geographic boundary. For example, if the user selects a nine iron and swings the nine iron such that the sensor module associated with the nine iron generates a pressure wave that is detected by the electronic device (e.g., a pressure wave that is indicative of an impact between the nine iron and an object), the electronic device can set the location at which the electronic device detected the pressure wave as the center point of the geographic boundary and can set the geographic radius to be a geographic radius associated with the nine iron. The geographic radius can be different depending on whether a distance between the location to a selected location of the golf course (e.g., a center point of the green for the golf hole currently being played) exceeds a threshold value. When the distance does not exceed the threshold, a first value can be used for the geographic radius, and when the distance does exceed the threshold, a second value can be used for the geographic radius. The threshold value can be specific to the type of golf club being used such that the threshold can be different, for example, if the user uses a driver or a nine iron.

While exemplary embodiments of the geographic boundary have been described as including a center point and a radius to form a circular geographic boundary, exemplary embodiments of the geographic boundary can have any suitable shape. For example, in exemplary embodiments of the present disclosure, the geographic boundary can be an ellipse, a rectangle, a triangle, a trapezoid, and/or any other suitable shape and/or an initial position within the geographic boundary can be set to any position within the boundary (e.g., offset from a center point). Furthermore, the shape of the geographic boundary can be different for different types of golf clubs.

In some embodiments, a false positive can be suppressed or ignored based on a time between detected impacts. The time criteria can be different for different golf clubs. As one example, the time period associated with a driver can be longer than the time period associated with a long iron, which can be longer than the time period associated with a short iron. In some embodiments, the first, intermediate, or last detected impact can be counted as the golf shot and the first detected impact can start the time period. The time period criteria can be used to advantageously eliminate false positives from practice shots (as well as from banging a golf club on the ground after a shot in frustration).

In some embodiments, a false positive can be suppressed or ignored based on a motion of the user. For example motion data of the electronic device in conjunction with GPS information can be used to determine if a user is moving when an impact is detected. Since it may take several seconds for the electronic device to detect a pressure wave from the sensor module after an impact, a history of motion data and location data can be maintained by the electronic device to allow the processing device to execute the environment to determine if the user was moving at the time of the impact. In order to accomplish this, the number of seconds since the impact occurred can be encoded in pressure wave generated by the sensor module. If it is determined that the user was moving at the time of the detected impact, the processing device 802 can be programmed to suppress or ignore the detected impact.

In some embodiments, a false positive can be suppressed or ignored based on criteria associated with an appropriateness of a golf club used for a given circumstance. The circumstance can take into account a location of the user with respect to the current hole or the next hole, a distance from the tee to the hole, and an appropriateness of the golf club can include an average distance a golf ball is hit by the user using a golf club, an intended use of the golf club (e.g., for long shots or short shots). As one example, if a user has putted on the current hole, and an impact is detected from a club that is not appropriate for another golf shot on the current hole or a tee shot on the next hole, the detected impact can be suppressed or ignored. For example, if the user hits their pitching wedge 110 yards on average and the next hole is a 175 yard par 3, any impact detected from the sensor module associated with the pitching wedge can be suppressed or ignored until after the next tee shot.

Figure 9:
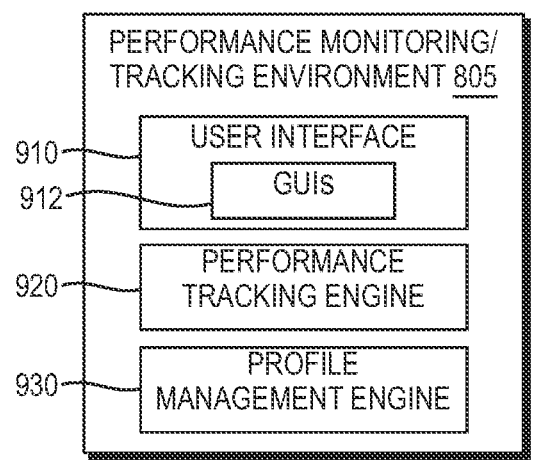
FIG. 9 is a block diagram of an exemplary embodiment of the performance monitoring and/or tracking environment that can be implemented in accordance with the present disclosure.

FIG. 9 is a block diagram of an exemplary embodiment of the performance monitoring and/or tracking environment 805 that can be implemented by embodiments of the electronic device 800 to monitor and/or track a user's golfing performance. The environment 805 can include a user interface 910, a profile management engine 920, and a performance tracking engine 930.

In exemplary embodiments, the user interface 910 can be programmed and/or include executable code to provide one or more graphical user interfaces (GUIs) 912 through which a user can interact with the environment 805. The GUIs 912 displayed to users can include data entry areas to receive information from the user and/or can include data outputs to display information to the user. Some examples of data entry fields include, but are not limited to text boxes, check boxes, buttons, dropdown menus, and/or any other suitable data entry fields.

The profile management engine 920 can be programmed and/or configured to receive, maintain, modify, and/or update a user profile. In exemplary embodiments, the user profile can be created by the user upon an initial execution of the environment 805. As one example, the processing device can execute the engine 920 to request user information including, for example, a user name, gender, weight, height, golf handicap, stance (e.g., right or left), an experience level (e.g., number of years playing, a number of rounds played in the previous year), and/or any other suitable user information. As another example, the processing device can execute the engine 920 to collect and/or setup instrument information including, for example, an identity of the instruments (e.g., different golf clubs) to which the sensor modules are or will be affixed, an association between the sensor modules and their corresponding instruments (e.g., golf clubs), an estimated distance an object (e.g., a golf ball) will likely travel when the user strikes it with each instrument, and/or any other suitable instrument information that can be utilized by the environment 805 to facilitate tracking and/or monitoring a user's performance during an activity (e.g., a round of golf). In exemplary embodiments, the user profile can be maintained, modified, and/or updated to include statistic information related to the user's past performance. In exemplary embodiments, the statistic information can include an average score, a handicap, an average distance an object travels for each of the instruments, a user performance on specific golf courses, and/or any other statistic information that can be utilized, maintained, and/or created based on the tracking and/or monitoring of a user's performance during an activity (e.g., a round of golf).

In exemplary embodiments, the performance tracking engine 930 can be programmed and/or configured to receive and/or maintain information corresponding to specific golf courses and/or holes at a specific golf course. For example, the engine 930 can receive and/or maintain a geographic map of the golf course including information related to the terrain of the golf course, a location of the holes on the golf course, a par for the holes on the golf course, and/or any other suitable information related to golf courses. In some embodiments, the golf course information can be maintained in a database of the remote system and the electronic device can request the golf course information from the database in response to an input from the user. In some embodiments, the golf course information can be stored on the electronic device executing the environment 805.

The performance tracking engine 930 can be executed by the processing device to monitor the electroacoustic transducer for detection of pressure waves propagating from the sensor modules associated with the golf clubs. For example, in exemplary embodiments, the pressure waves propagating from the sensor modules can include information corresponding to accelerometer information of the golf club, an indication of an impact between a golf club and an object (e.g., a golf ball or the earth), an indication of a golf shot, swing analysis information (e.g., a swing speed, a swing tempo, swing force, club face angle, swing plane, etc., represented via accelerometer output information), and/or any other suitable information related to an operation of the sensor module and/or a utilization of the instrument. The information received by the electronic device can be utilized upon execution of the engine 930 to identify a location at which a golf shot occurred, identify a number of golf shots that occurred for a particular hole, identify a golf score for a particular hole or course, provide a swing analysis, identify false positive impacts/golf shots (e.g., using criteria described herein), and the like. The information received from the pressure waves can also be provided to the engine 920 to create, update, and/or modify statistic information in the user profile.

FIGS. 10-32 provide exemplary GUIs that can be rendered on a display of an electronic device in response to an execution of the environment 805 by the electronic device 800 shown in FIG. 8.

Figure 10:
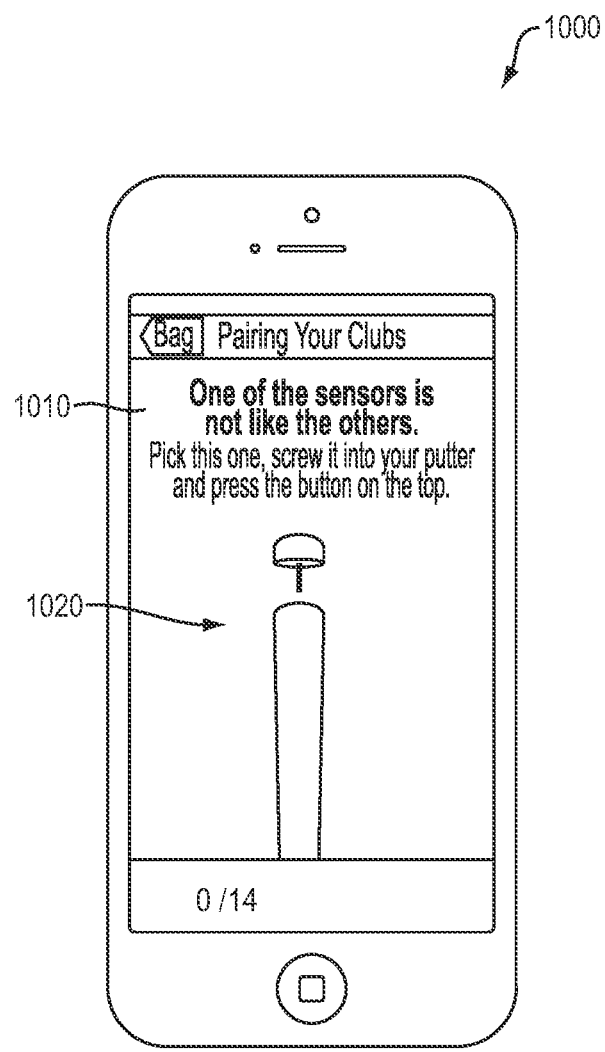
FIGS. 10-15 show exemplary graphical user interfaces that can be provided in accordance with exemplary embodiments of the present disclosure.

FIG. 10 shows an exemplary GUI 1000 that can be provided by exemplary embodiments of the environment 805 to facilitate a recognition process between an electronic device and sensor modules. The GUI 1000 renders an instructional screen 1010 on the display of the electronic device indicating that the putter is ready to be associated with a sensor module. In exemplary embodiments where the sensor modules are affixed to the golf clubs, the housing of the remaining sensor modules to be used for other golf clubs. The screen 1010 can instruct the user of this difference and can display a graphic or animation illustrating how to affix the sensor module to the golf club. The screen 1010 can also instruct the user to initiate the recognition process by depressing the push button (i.e. switch) on the sensor module, which causes the sensor module to generate a pressure wave that can be detected by the user's electronic device (e.g., smart phone) to associate the sensor module with the electronic device based on a characteristic or parameter associated with the pressure wave (e.g., a frequency of the pressure wave, a unique identifier included in the pressure wave).

Figure 11:
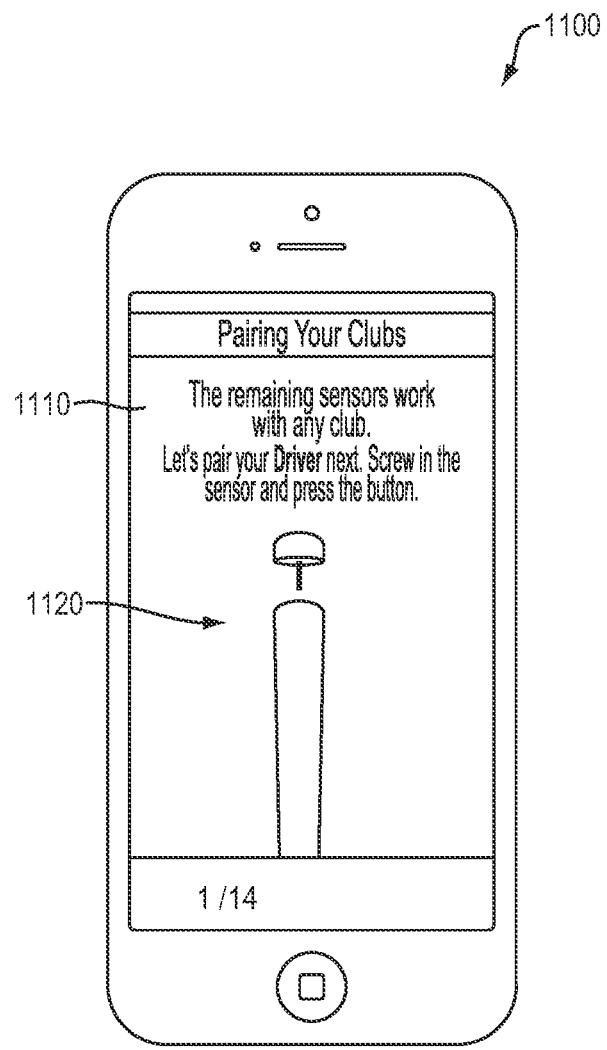

FIG. 11 shows an exemplary GUI 1100 that can be provided by exemplary embodiments of the environment 805 to facilitate a recognition process between an electronic device and sensor modules. The GUI 1100 renders an instructional screen 1110 on the display of the electronic device indicating that a golf club (e.g., other than the putter) is ready to be associated with a sensor module. For embodiments where the sensor modules are affixed to the golf clubs, the screen 1110 can display a graphic or animation illustrating how to affix the sensor module to the golf club and can instruct the user to initiate the recognition process by depressing the push button (i.e. switch) on the sensor module, which causes the sensor module to generate a pressure wave that can be received by the user's electronic device (e.g., smart phone) to associate the sensor module with the electronic device based on a characteristic or parameter of the pressure wave (e.g., a frequency of the pressure wave, a unique identifier included in the pressure wave.

Figure 12:
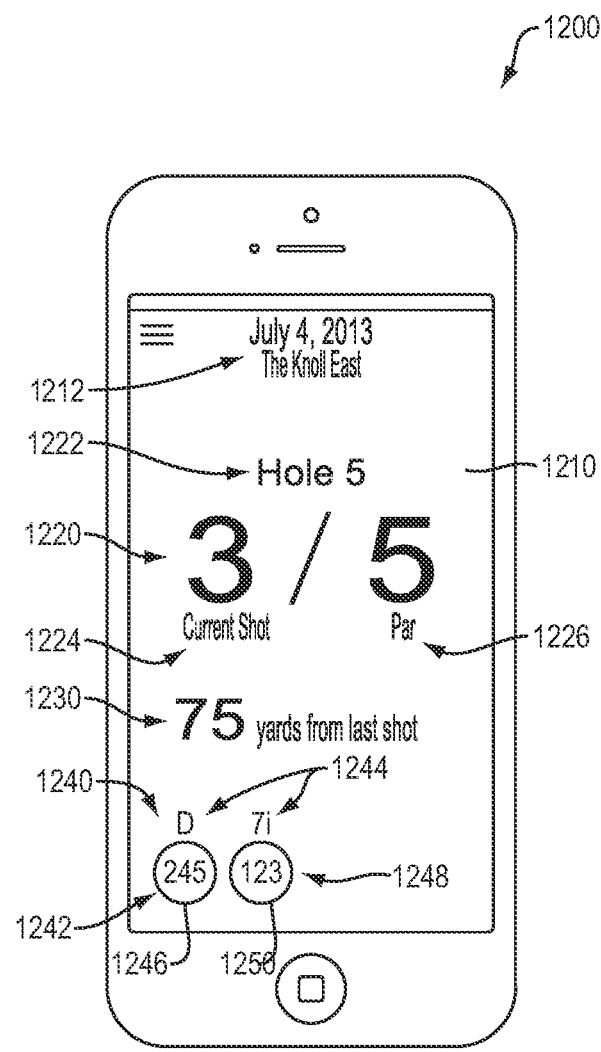

FIG. 12 shows an exemplary GUI 1200 that can be provided by exemplary embodiments of the environment 805 to render a screen 1210 on the display of an electronic device related to the monitoring and/or tracking of the user's performance during a round of golf. The screen 1210 can identify a date 1212 on which the round is being played, current hole information 1220, a distance 1230 from the last golf shot by the user, and previous shot information 1240. The current hole information 1220 can identify the current hole 1222 being played, a number of golf shots 1224 taken by the user on the hole, and a number of shots 1226 corresponding to par for the hole. As one example, as shown in FIG. 12, information about the user's first shot 1242 on the current hole 1222 can be graphically depicted to indicate a type 1244 of golf club used by the user to take the first shot, which is shown as a "D" to indicate that the driver was used to take the first shot, and can include a distance 1246 in yards that the first shot traveled. As another example, as shown in FIG. 12, information about the user's second shot 1248 on the current hole 1222 can be graphically depicted to indicate the type 1244 of golf club used by the user to take the second shot, which is shown as "7i" to indicate that the seven iron was used to take the second shot, and can include a distance 1250 in yards that the second shot traveled.

As described herein, the number of golf shots taken by the user can be determined based on pressure waves propagating from a sensor module associated with the golf club that are detected by the user's electronic device. The current hole 1220 can be determined by the users geographic location on the golf course compared to golf course information including a geographic layout of the golf course, which can used by the environment 805 to automatically update the current hole information and the par information for the current hole. The distance 1230 from the last shot can be determined, using the user's GPS enabled electronic device, based on a location of the user's electronic device during the impact portion of the user's last shot and the current geographic location of the user's electronic device or the geographic location of the user's electronic device when the user strikes the golf ball on the shot after the last shot.

Figure 13:
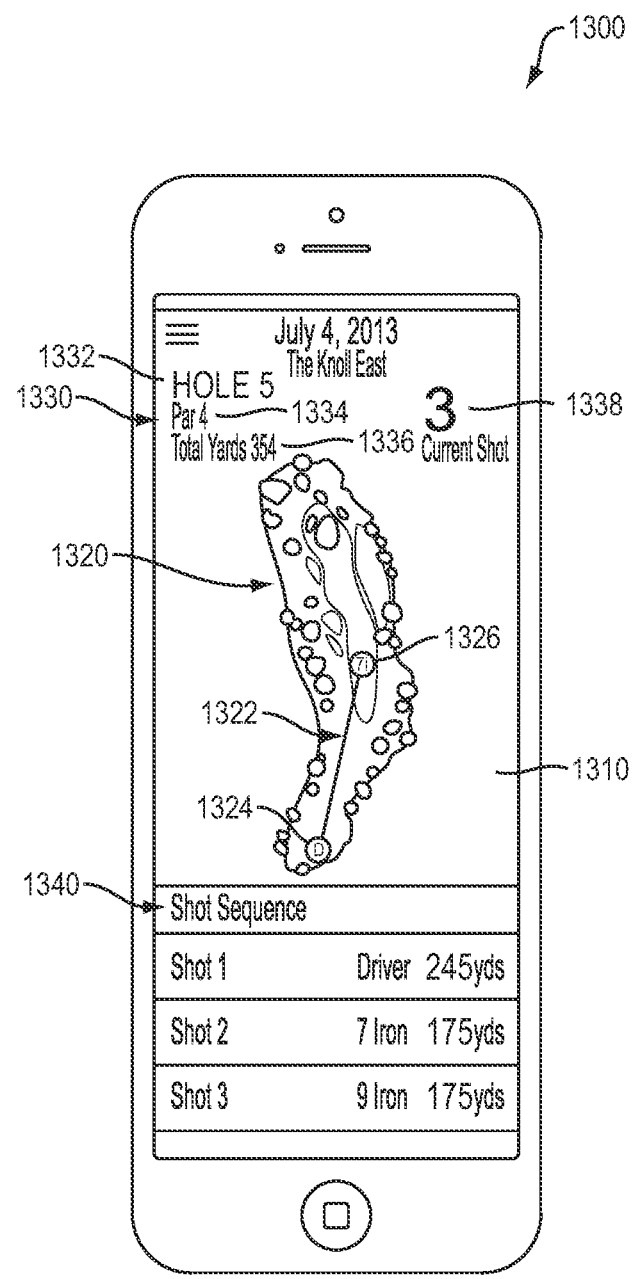

FIG. 13 shows an exemplary GUI 1300 that can be provided by exemplary embodiments of the environment 805 to render a screen 1310 on a display of an electronic device related to the monitoring and/or tracking of the user's performance during a round of golf. The screen 1310 can display a geographic map 1320 of the hole, current hole information 1330, and a shot sequence 1340. The geographic map 1320 can display a terrain of the golf course. A user's shot performance 1322 for the hole can be overlaid on the geographic map 1320. For example, the shot performance 1322 can include a marker 1324 overlaid on the geographic map 1320 at a first location to indicate the first shot taken by the user for the hole and the type of golf club used by the user for the first shot (e.g., shown as a "D" to indicate that the driver was used) and a marker 1326 overlaid on the geographic map 1320 at a second location to indicate the second shot taken by the user for the hole and the type of golf club used by the user for the first shot (e.g., shown as a "7i" to indicate that the seven iron was used) The current hole information 1330 can include a current hole number 1332, par for the hole 1334, a total number of yards for the hole 1336, and the current number of shots taken by the user 1338. The shot sequence information can list the shots taken by the user for the hole and can identify the type of golf club used to take the shots and the distance that the shots traveled.

Figure 14:
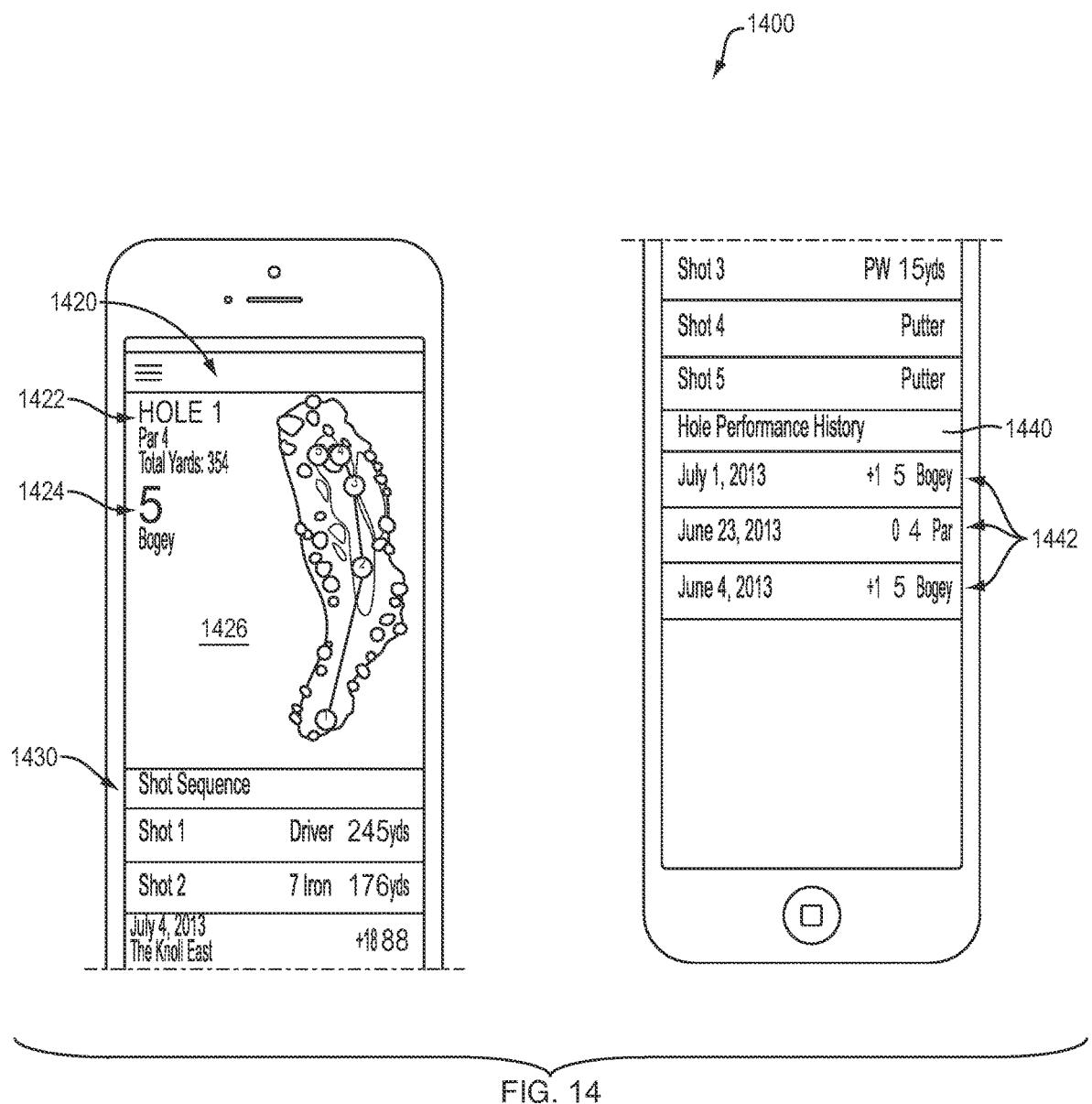

FIG. 14 shows an exemplary GUI 1400 that can be provided by exemplary embodiments of the environment 805 to render, on a display of an electronic device, hole information 1420 for a selected hole in a selected round of golf monitored and/or tracked by the environment 805. The hole information 1420 can include course specified information 1422 (e.g., a hole number, par, and distance), a number of shots 1424 the user took for the hole, a geographic map 1426 for the hole overlaid with the golf shots taken by the user for the hole, a shot sequence 1430, and a hole performance history 1440. The hole performance history 1440 can include a list 1442 of dates for which the hole was played by the user and a number golf shots taken by the user on the hole for each date.

Figure 15:
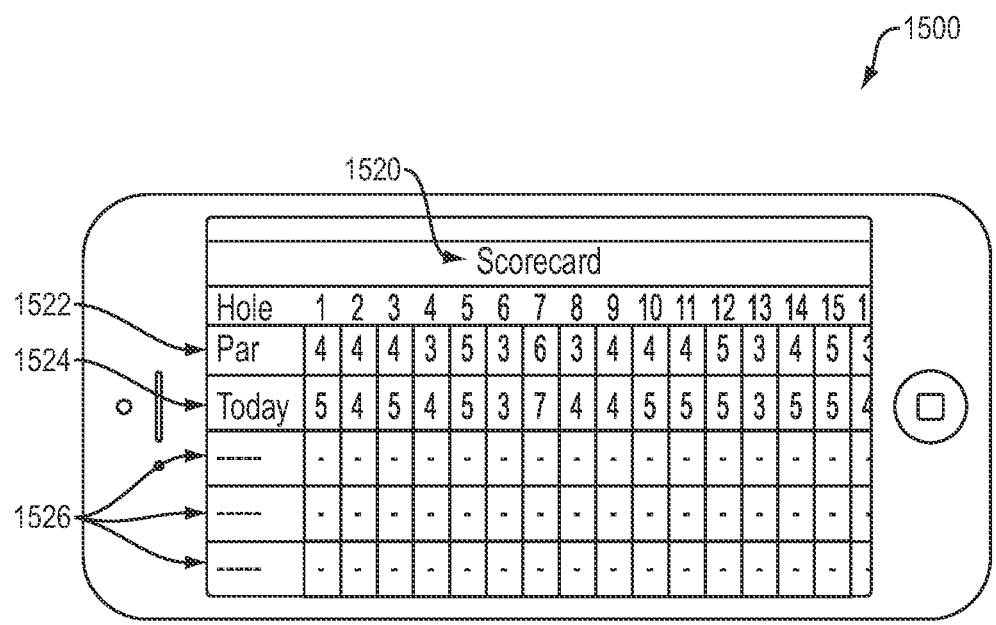

FIG. 15 shows an exemplary GUI 1500 that can be provided by exemplary embodiments of the environment 805 to render, on a display of an electronic device, a golf score history 1520 for a selected golf course. The golf score history 1520 can be in the form of a scorecard that provides the par 1522 for each hole, the number of golf shots 1524 taken by the user for each hole during the most recent round of golf, and the number of golf shots 1526 taken by the user for additional rounds of golf played by the user in the past.

Figure 16:
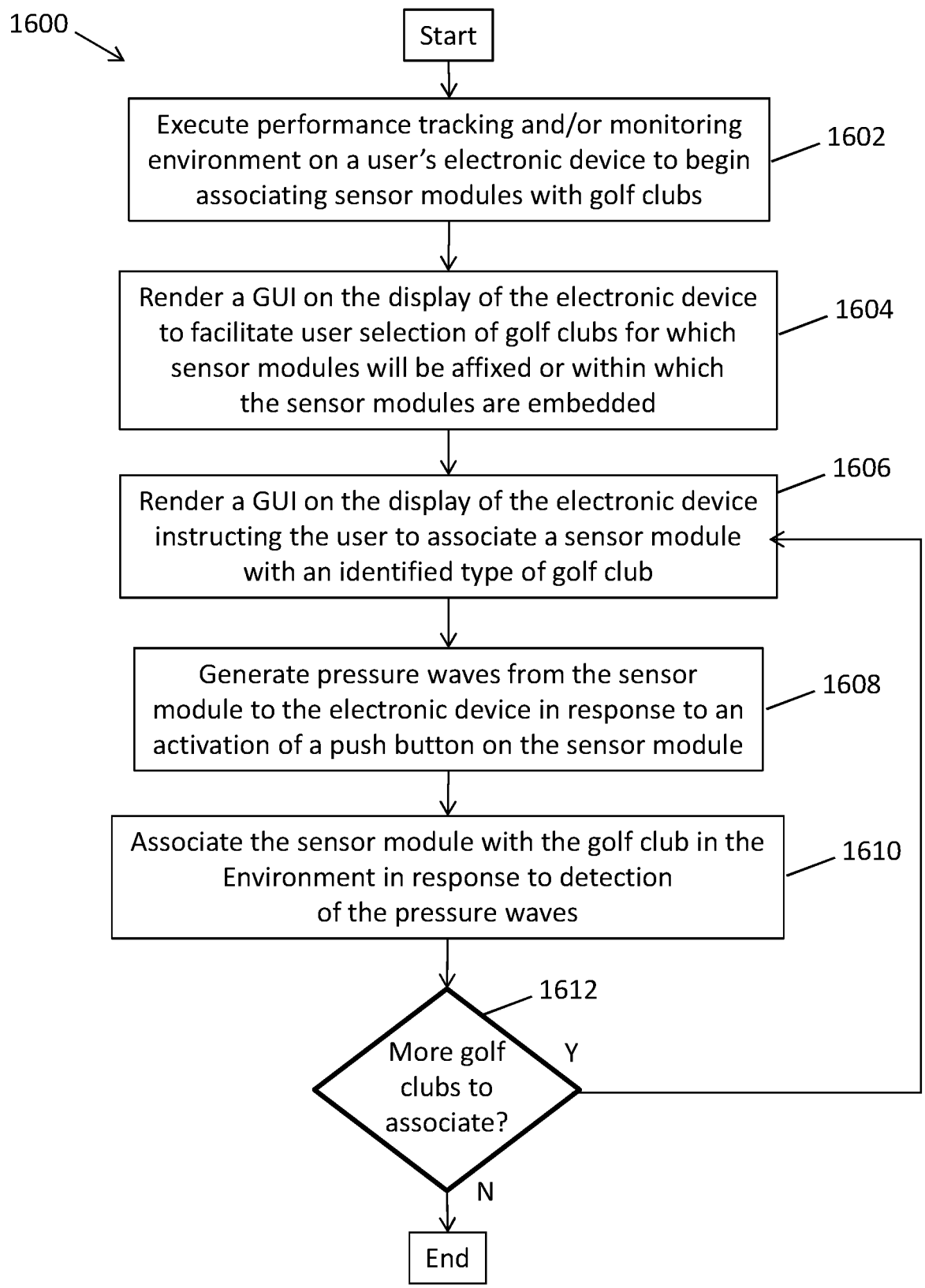
FIG. 16 is a flowchart illustrating a process for associating a golf club with a sensor module by exemplary embodiments of the environment.

FIG. 16 is a flowchart illustrating a process 1600 for associating a golf club with a sensor module by exemplary embodiments of the environment 805. To begin, the electronic device can execute an embodiment of the performance tracking and/or monitoring environment 805 to initiate the association process at step 1602. In response to the initiation of the association process, at step 1604, the environment 805 can be executed by the electronic device to render a GUI on the display of the electronic device to facilitate user selection of golf clubs from a list of golf clubs for which sensor modules will be affixed and/or within which the sensor modules are embedded. At step 1606, after a user has selected the golf clubs from the list, the environment 805 can be executed by the electronic device to render a GUI on the display of the electronic device instructing the user to affix a sensor module to a golf club identified by the GUI or locate the golf club within which a sensor module is embedded (e.g., via text and/or graphics). The GUI can also instruct the user to actuate a button on the sensor module to associate the sensor module with the electronic device and/or to associate the sensor module with the golf club in the environment 805. At step 1608, the sensor module can generate pressure waves in response to actuation of the button on the sensor module.

At step 1610, the electronic device can detect the pressure waves propagating from the sensor module and can execute the environment 805 to associate the sensor module with the electronic device and/or to associate the sensor module with the identified golf club (e.g., store an associate between the sensor module and the golf club displayed at step 1606). At step 1612, the electronic device can execute the environment 805 to determine whether the user selected additional golf clubs to be associated. If so, the process 1600 repeats from step 1606. If not, the process 1600 ends.

Figure 17:
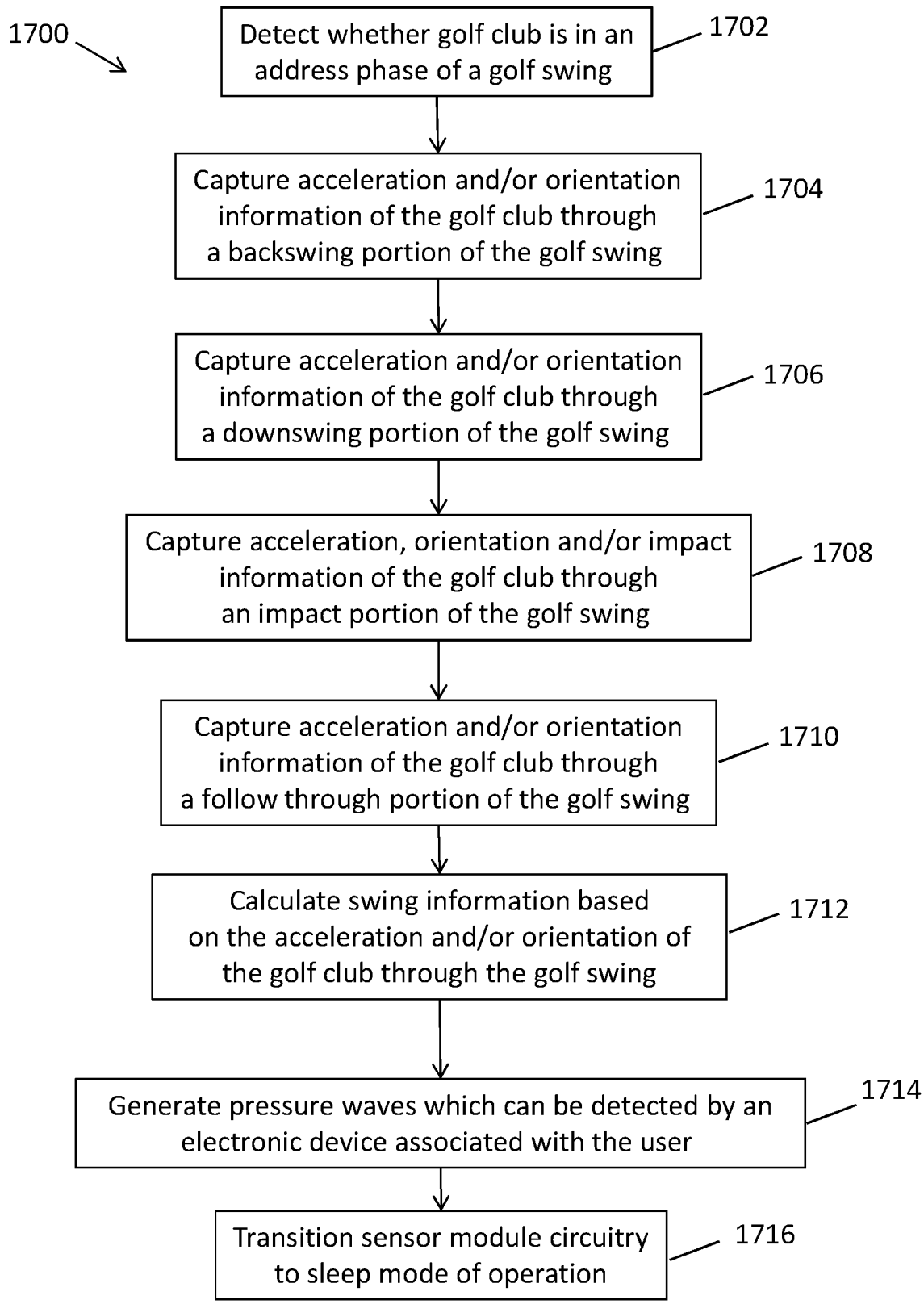
FIG. 17 is a flowchart illustrating a process that can be implemented by exemplary embodiments of the sensor module circuitry during a swing event.

FIG. 17 is a flowchart illustrating a process 1700 that can be implemented by exemplary embodiments of the sensor module circuitry 212 during a swing event. At step 1702, the sensor module circuitry can detect that the golf club is in an address phase of a golf swing. For example, the accelerometer and/or gyroscope of the sensor module circuitry can output signals that can be processed by the sensor module circuitry to determine that the golf club has an orientation that is within the addressing range. At step 1704, the sensor module circuitry can capture acceleration and/or orientation information of the golf club (e.g., based on an acceleration and/or orientation of the sensor module affixed to and/or embedded within the golf club) through a backswing portion of the golf swing. At step 1706, the sensor module circuitry can capture acceleration and/or orientation information of the golf club through a downswing portion of the golf swing. At step 1708, the sensor module circuitry can capture acceleration, orientation, and/or impact information of the golf club through an impact portion of the golf swing. In exemplary embodiments, the impact information can be captured as descried herein. At step 1710, the sensor module circuitry can capture acceleration and/or orientation information of the golf club through a follow-through portion of the golf swing.

At step 1712, the sensor module circuitry can calculate, derive, and/or identify swing information utilizing the acceleration, orientation, and/or impact information captured before, during, and/or after the golf swing. For example, the processing device of the sensor module circuitry can execute the swing monitoring system to calculate a swing tempo, swing velocity, swing force, club face angle, swing plane, impact force, and/or any other swing parameters or other swing analysis parameters and/or to identify a golf shot based on the impact information. At step 1714, the sensor module circuitry can generate pressure waves, which can be detected by an electroacoustic transducer of an electronic device associated with the user, and at step 1716, the sensor module circuitry can transition from a normal mode of operation to a sleep mode of operation.

Figure 18:
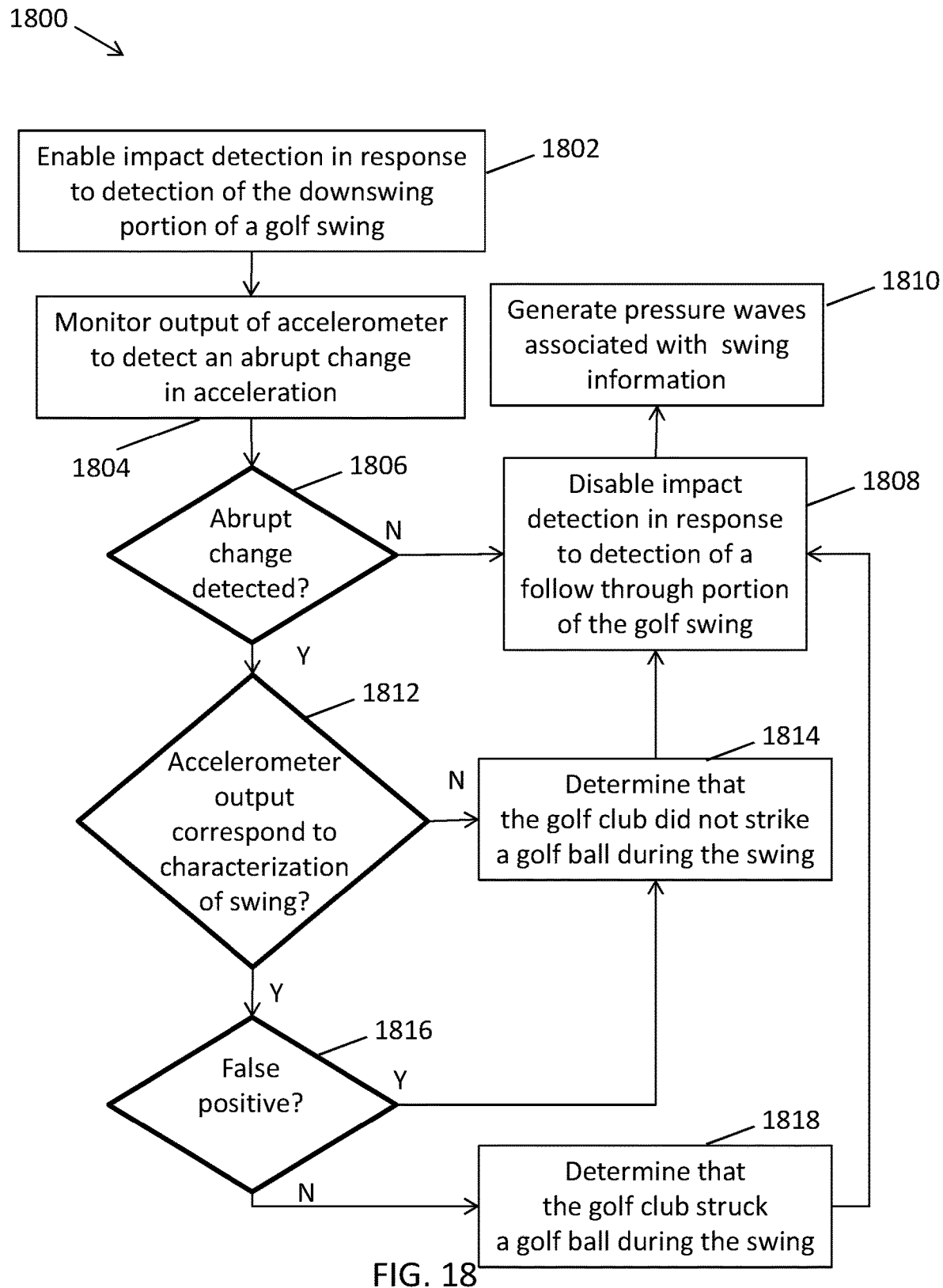
FIG. 18 is a flowchart of a process that can be implemented by exemplary embodiments of the sensor module circuitry to detect an impact during a golf swing.

FIG. 18 is a flowchart of a process 1800 that can be implemented by exemplary embodiments of the sensor module circuitry to detect an impact during a golf swing. At step 1802, the sensor module circuitry can enable impact detection in response to detection of a downswing portion of the golf swing and at step 1804, the sensor module circuitry can monitor the accelerometer for an abrupt change in acceleration. At step 1806, the sensor module circuitry can determine whether an impact occurred based on an abrupt change in acceleration. If no abrupt change is detected, the sensor module circuitry disables impact detection in response to detection of a follow-through portion of the golf swing at step 1808 and generates pressure waves propagating through air, which can be detected by an electroacoustic transducer of the user's electronic device at step 1810. If an abrupt change in acceleration is detected, the sensor module circuitry can determine whether the impact is the result of a golf swing by analyzing the output of the accelerometer immediately prior to and immediately after an impact is detected to determine whether the accelerometer output corresponds to characterized swing information at step 1812. If not, the sensor module circuitry determines that the golf club did not strike a golf ball during the swing at step 1814 and the process proceeds to step 1808. If it is determined by the circuitry that the accelerometer output corresponds to characterized swing information, the sensor module circuitry determines whether the impact is a false positive using techniques and criteria described herein. If it is determined by the circuitry that the impact is a false positive, the process proceeds to step 1816. If not, the circuitry determines that the golf club struck a golf ball during a swing at step 1818 and the process proceeds to step 1808.

Figure 19:
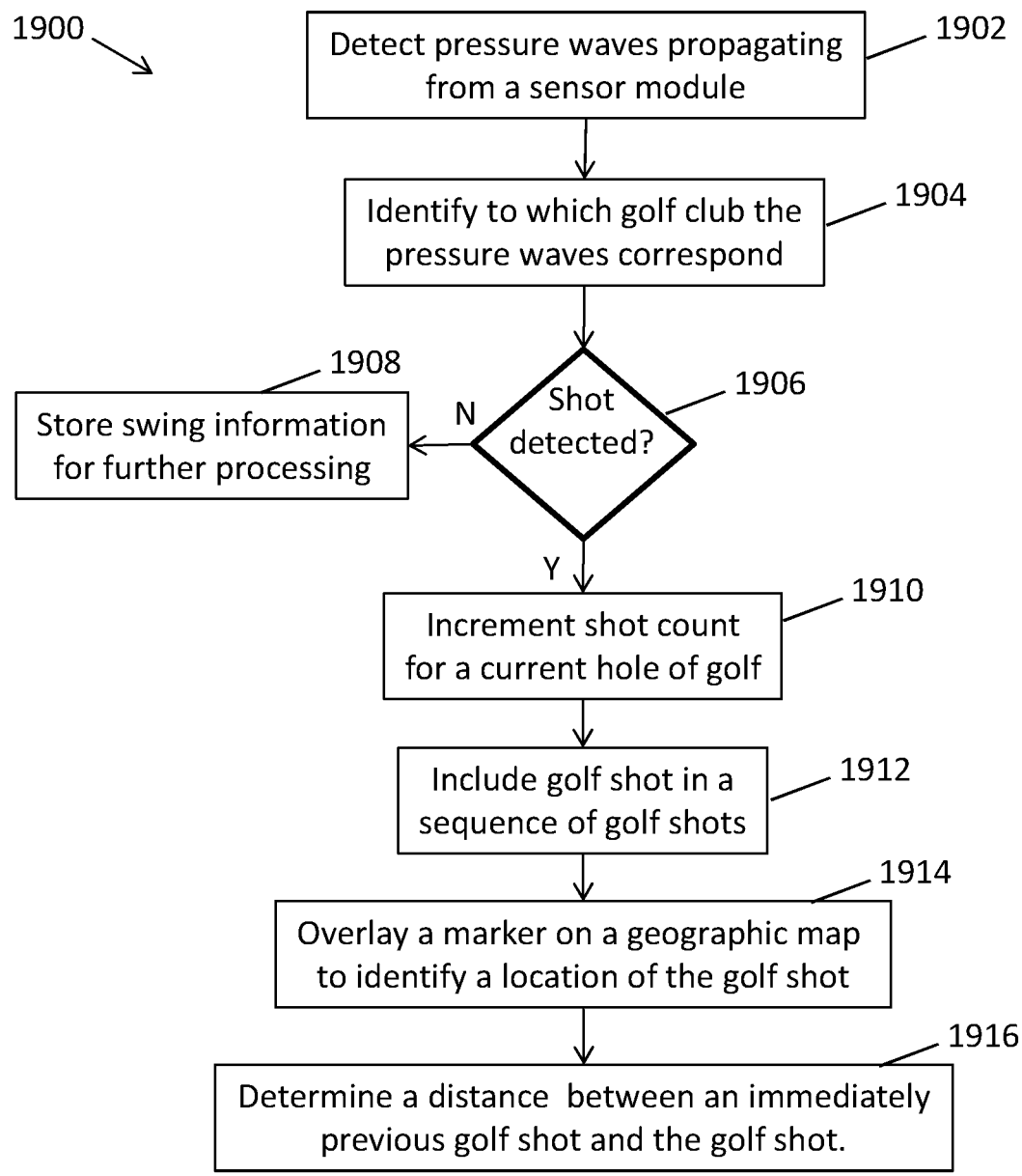
FIG. 19 is a flowchart illustrating a process that can be implemented by an electronic device executing an exemplary embodiment of the monitoring and/or tracking environment.

FIG. 19 is a flowchart illustrating a process 1900 that can be implemented by an electronic device executing an exemplary embodiment of the monitoring and/or tracking environment described herein. At step 1902, the electronic device can detect the pressure waves propagated by a sensor module affixed to or embedded in a golf club. At step 1904, the electronic device can execute the environment 805 to identify from which sensor module the pressure waves propagate and determine which golf club corresponds to the sensor module. For example, a recognition process may have been executed previously to associate a golf club to the sensor module in the environment 805 and the electronic device can execute the environment 805 to search and/or look-up the association corresponding a parameter of the pressure waves (e.g., frequency) and/or an identification parameter included in the pressure wave (e.g., using modulation). At step 1906, the electronic device can execute the environment 805 to determine whether the pressure waves are indicative of a golf shot (e.g., using false positive detection techniques and criteria described herein). If not, the electronic device can store the information/data extracted from the pressure waves for further processing at step 1908. If the information/data extracted from the pressure waves is indicative of a golf shot, the electronic device can execute the environment 805 to register a golf shot and can increment a shot counter for a current hole of golf being monitored and/or tracked using the environment 805 at step 1910. At step 1912, the golf shot can be included in a sequence of golf shots for the current hole and at step 1914, a marker can be overlaid on a geographic map to identify a location of the golf shot. At step 1916, a distance between an immediately previous golf shot and the present golf shot can be determined (e.g., based on a location of the user's GPS enabled electronic device for the previous shot and the present shot.)

Figure 20:
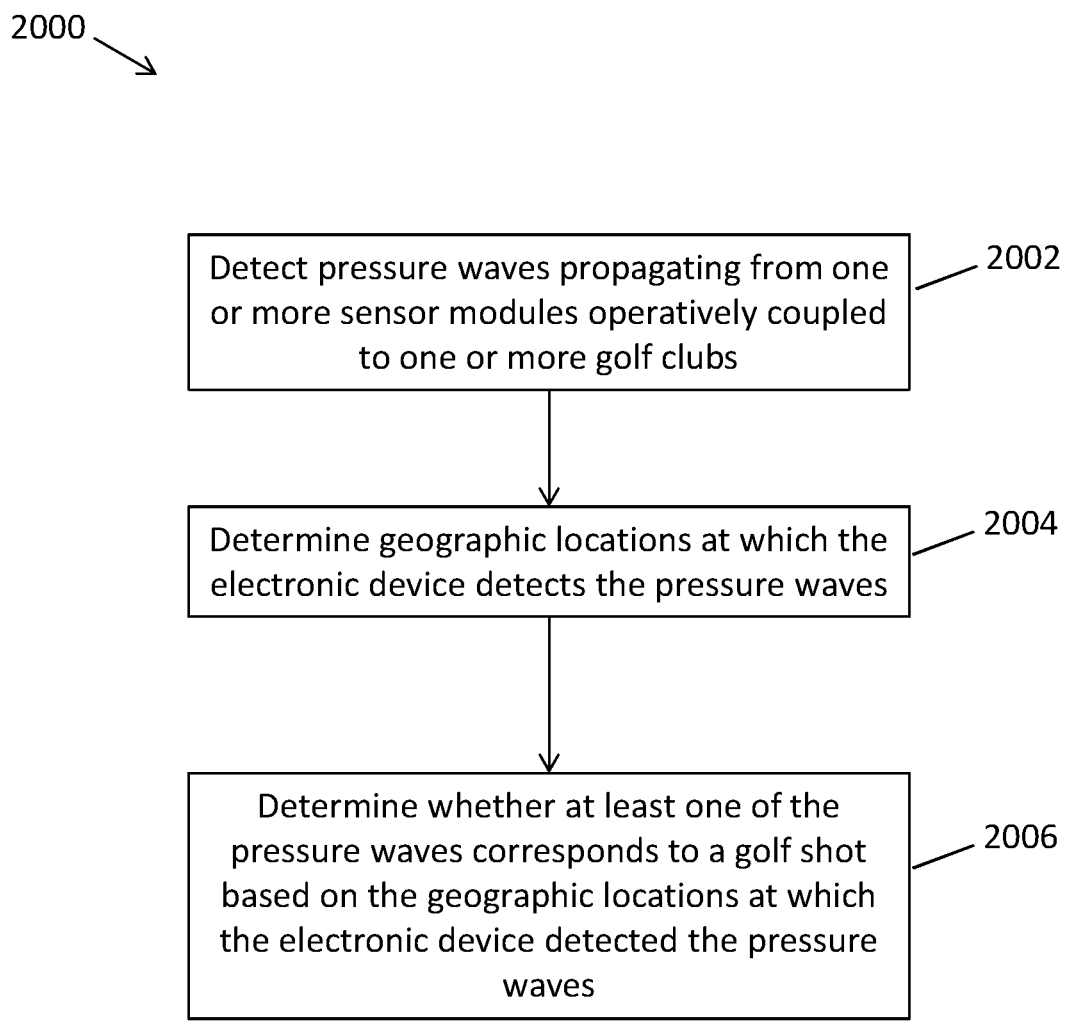
FIG. 20 is a flowchart illustrating a process that can be implemented in accordance with exemplary embodiments of the present disclosure to determine whether a golf shot occurred during a round of golf based on geographic location data.

FIG. 20 is a flowchart illustrating a process 2000 that can be implemented by an electronic device executing an exemplary embodiment of the monitoring and/or tracking environment 805 to determine whether a golf shot occurred during a round of golf based on geographic location data. At step 2002, the electroacoustic transducer of the electronic device can detect pressure waves from one or more sensor modules operatively coupled to one or more golf clubs. The pressure waves can include or represent information associated with an acceleration of the golf clubs to which the one or more sensor modules are secured and/or embedded and/or can include or represent indications of impacts between the golf clubs and object. As one example, the pressure waves can be modulated to include acceleration information output by the accelerometer, which can be detected by the electroacoustic transducer of the electronic device, and can be processed by the electronic device upon execution of the environment 805 to determine whether the acceleration data corresponds to an impact between the corresponding golf club and an object (e.g., the earth, a golf ball, etc.). As another example, the pressure waves can be modulated to include an indication that the sensor module detected an impact between the corresponding golf club and an object. At step 2004, the electronic device can determine geographic locations at which the electronic device detected the pressure waves. For example, the GPS receiver of the electronic device can receive GPS data in broadcasts from the GPS satellite and the electronic device can use the GPS data in the broadcasts to determine a geographic location (e.g., longitude and latitude) of the electronic device at the time the pressure waves are detect (or before or after the pressure waves are detected) by the electronic device.

At step 2006 the processing device of the electronic device can determine whether at least one of the pressure waves corresponds to a golf shot based on the geographic locations at which the electronic device detected the pressure waves. In some embodiments, a geographic boundary can be established by the electronic device based on a geographic location at which the electronic device detects a specified pressure wave (e.g., the geographic location can form a center point of the geographic boundary). For example, the specified one of the pressure waves corresponds to a first one of the separately generated pressure waves detected by the electronic device after a previous golf shot is identified as counting towards a golf score as described herein. The electronic device can set a radius of the geographic boundary from the center point such that the geographic boundary encircles the center point. In some embodiments, the radius of the geographic boundary can be set based on the golf club type associated with the specified one of the pressure waves used to generate the center point of the geographic boundary and/or based on a distance between the center point of the geographic boundary and a specified location of the golf course. For example, each type of golf club can be associated with multiple radius values, e.g., a first radius value when the center point of the geographic boundary exceeds a threshold distance from a selected golf course location (e.g., the center of the green), and a second radius value when the center point of the geographic boundary is within the threshold distance from the selected golf course location (e.g., the center of the green). The type of golf club associated with the specified one of the pressure waves can be determined by the electronic device based on, for example, a unique identifier included in or represented by the specified one of the pressure waves that associates a particular sensor module with a corresponding golf club.

To determine whether at least one of the pressure waves corresponds to a golf shot, the electronic device can determine whether the other geographic locations at which the electronic device detected the pressure waves are within the geographic boundary. Upon determining that one of the geographic location of one of the pressure waves is outside of the geographic boundary, the electronic device can select one of the geographic locations of the electronic device within the geographic boundary as a golf shot location for the golf shot and can ignore the other geographic locations of the electronic device within the geographic boundary that were not selected as the golf shot location. For example, the electronic device can select the center point of the geographic boundary, the last geographic location at which the electronic device detected a last one of the pressure waves within the geographic boundary, and/or any of the other geographic locations at which the electronic device detected a pressure wave within the geographic boundary.

In some embodiments, the electronic device determine whether at least one of the separately generated pressures corresponds to a golf shot based on the geographic locations at which the electronic device detected the separately generated pressure waves and a temporal relationship of the separately generated pressure waves detected by the electronic device. As one example, the temporal relationship can correspond to a time between detection of the separately generated pressure waves by the electronic device such that at least one separately generated pressure wave is ignored when consecutively generated pressure waves are detected within a specified time period. As another example, the temporal relationship corresponds to a specified time period, and the electronic device can determine whether at least one of the separately generated pressure waves corresponds to a golf shot by determining whether the electronic device detected the separately generated pressure waves within specified time period.

Figure 21:
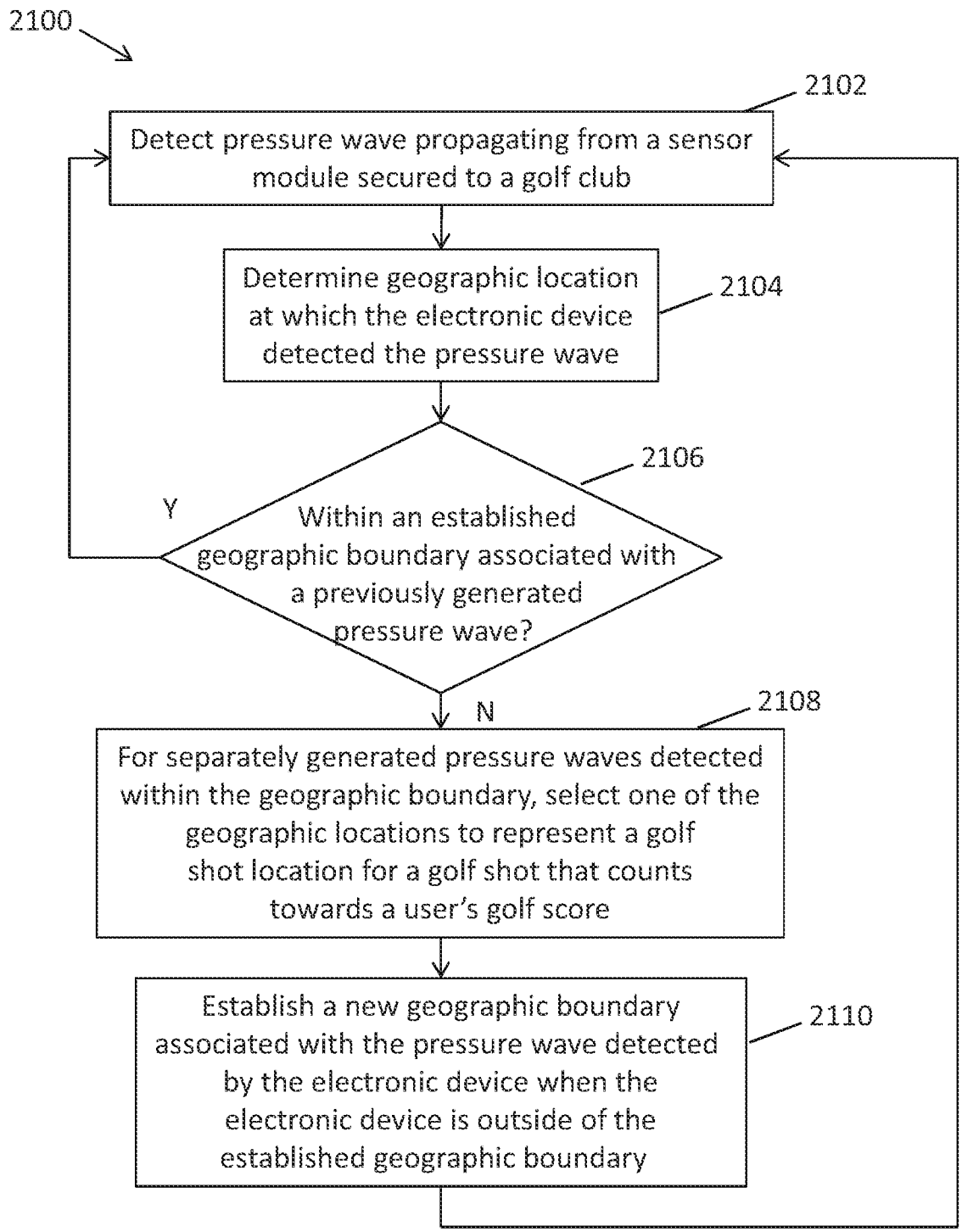
FIG. 21 is a flowchart illustrating another process that can be implemented in accordance with exemplary embodiments of the present disclosure to determine whether a golf shot occurred during a round of golf based on geographic location data.

FIG. 21 is a flowchart illustrating a process 2100 that can be implemented by an electronic device executing an exemplary embodiment of the monitoring and/or tracking environment 805 to determine whether a golf shot occurred during a round of golf. At step 2102, the electroacoustic transducer of the electronic device can detect a pressure wave from a sensor module secured to or embedded within a golf club as described herein. At step 2104, the electronic device can determine a geographic location at which the electronic device detected the pressure wave. For example, the electronic device can receive a GPS data from a GPS satellite via the GPS receiver and can determine the geographic coordinates (e.g., longitude and latitude) of the electronic device based on the received GPS data. At step 2106, the electronic device determines whether the geographical location (e.g., longitude and latitude) at which the electronic device detected the pressure wave is within an established geographic boundary. If so, the process 2100 repeats from step 2102. If not, at step 2108, for the pressure wave detected by the electronic device within the established geographic boundary, the processing device of electronic device can select one of the geographic locations (e.g., the geographic location associated with the first, intermediate, or last separately generated pressure wave that was detected while the electronic device was within the geographic boundary) to represent a golf shot location for a golf shot that counts towards a user's golf score. At step 2110, the processing device of the electronic device can establish a new geographic boundary based on detection, at a geographic location outside of the established geographic boundary, of a subsequent pressure wave by the electronic device propagating from a sensor module secured to and/or embedded within a golf club. For example, the electronic device can set a center point of the new geographic boundary to be the geographic location outside the established geographic boundary at which the electronic device detected the pressure wave, and can set a radius of the geographic boundary to a radius value based on an identification of the golf club to which the sensor module that generated the subsequent pressure wave is secured and/or embedded within and/or based on a distance of the center point to a select location on the golf course.

Figure 22:
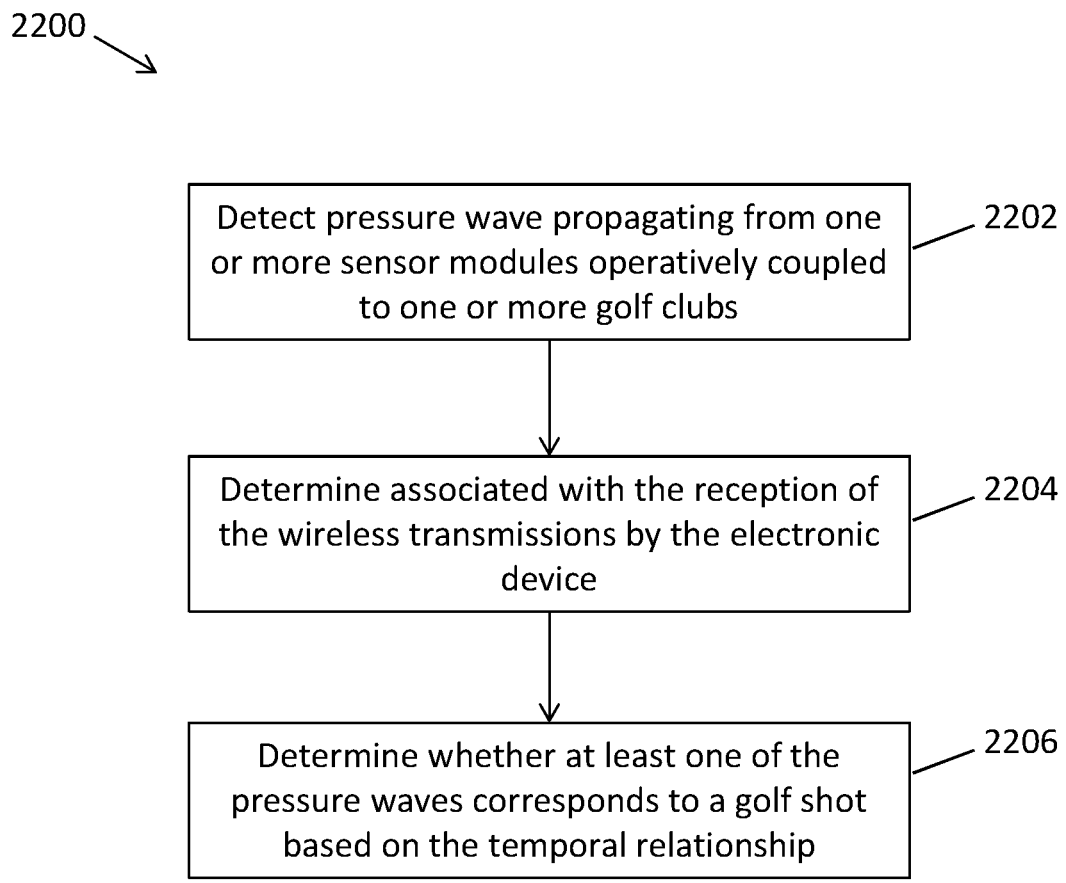
FIG. 22 is a flowchart illustrating a process that can be implemented in accordance with exemplary embodiments of the present disclosure to determine whether a golf shot occurred during a round of golf based on a temporal relationship of time-related reception data.

FIG. 22 is a flowchart illustrating a process 2200 that can be implemented by an electronic device executing an exemplary embodiment of the monitoring and/or tracking environment 805 to determine whether a golf shot occurred during a round of golf. At step 2202, separately generated pressure waves are detected, by the electroacoustic transducer of the electronic device, from one or more sensor modules operatively coupled to one or more golf clubs as described herein. At step 2204, the processing device of the electronic device can determine a temporal relationship associated with the detection of the separately generated pressure waves by the electronic device. At step 2206, the processing device of the electronic device can determine whether at least one of the separately generated pressure waves corresponds to a golf shot based on the temporal relationship of detection of the separately generated pressure waves. For example, the processing device of the electronic device can determine whether at least one of the separately generated pressure waves corresponds to a golf shot based on a time between detection of the separately generated pressure waves and/or whether the electronic device detected the separately generated pressure waves within specified time period. In some embodiments, if consecutively generated pressure waves are detected within a specified time of each other, the processing device of the electronic device can ignore one or more of the separately generated pressure waves when determining whether a golf shot occurred. In some embodiments, the processing device of the electronic device can define a time period that begins upon detection of a first pressure. The first pressure wave and subsequent pressure waves detected within the time period can be analyzed with respect to locations at which the electronic device detected the separately generated pressure waves to determine whether one or more the separately generated pressure waves are associated with one or more golf shots.

In describing exemplary embodiments, specific terminology is used for the sake of clarity. For purposes of description, each specific term is intended to at least include all technical and functional equivalents that operate in a similar manner to accomplish a similar purpose. Additionally, in some instances where a particular exemplary embodiment includes a plurality of system elements, device components or method steps, those elements, components or steps may be replaced with a single element, component or step. Likewise, a single element, component or step may be replaced with a plurality of elements, components or steps that serve the same purpose. Moreover, while exemplary embodiments have been shown and described with references to particular embodiments thereof, those of ordinary skill in the art will understand that various substitutions and alterations in form and detail may be made therein without departing from the scope of the invention. Further still, other embodiments, functions and advantages are also within the scope of the invention.

Exemplary flowcharts are provided herein for illustrative purposes and are non-limiting examples of methods. One of ordinary skill in the art will recognize that exemplary methods may include more or fewer steps than those illustrated in the exemplary flowcharts, and that the steps in the exemplary flowcharts may be performed in a different order than the order shown in the illustrative flowcharts.

The invention claimed is:

1. A sensor module adapted to be affixed to or embedded in a golf club, the sensor module comprising:
sensor circuitry including at least one sensor that is operable to generate one or more outputs in response to usage of the golf club;
an electromechanical device operable to generate a pressure wave that propagates through air; and
control circuitry, the control circuitry being operatively coupled to the sensor circuitry and the electromechanical device, the control circuitry being configured to (i) detect the usage of the golf club based on the one or more outputs of the sensor circuitry and, (ii) control the electromechanical device to move the electromechanical device to generate the pressure wave in response to detection of the usage of the golf club,
wherein a parameter of the pressure wave identifies the golf club.

2. The sensor module of claim 1, wherein the pressure wave is effective to convey swing analysis information to the remote electronic device.

3. The sensor module of claim 1, wherein the parameter of the pressure wave is effective to differentiate the golf club being used from other golf clubs.

4. The sensor module of claim 1, wherein the pressure wave includes at least one characteristic of a swing of the golf club.

5. The sensor module of claim 1, wherein a plurality of pressure waves are generated and a timing of the generation of the plurality of pressure waves is based on usage of the golf club.

6. The sensor module of claim 5, wherein at least one of the plurality of pressure waves is generated after an impact between the golf club and an object is detected.

7. The sensor module of claim 5, wherein at least one of the plurality of pressure waves is generated after a golf swing is completed.

8. The sensor module of claim 1, wherein the pressure wave lasts for a duration of less than one second.

9. The sensor module of claim 8, wherein the pressure wave has a frequency between approximately fifteen kilohertz and approximately twenty-five kilohertz.

10. The sensor module of claim 1, wherein the electromechanical device includes a speaker for generating the pressure wave.

11. The sensor module of claim 1, wherein a frequency at which the pressure wave propagates uniquely identifies the golf club.

12. The sensor module of claim 1, wherein the control circuitry includes a processing device.

13. The sensor module of claim 1, wherein the control circuitry controls the electromechanical device to modulate the movement of the electromechanical device to encode an indication that an impact has been detected during a golf swing.

14. The sensor module of claim 1, wherein the sensor circuitry includes an accelerometer and the control circuitry determines whether the usage of the golf club corresponds to a golf shot or a false positive based on acceleration data output by the accelerometer.

15. A method of monitoring a golf club for a golf shot, comprising:
sensing, via sensor circuitry of a sensor module, usage of the golf club;
generating one or more outputs from the sensor circuitry in response to usage of the golf club;
detecting, via control circuitry, the usage of the golf club based on the one or more outputs of the sensor circuitry; and
controlling, by the control circuitry, an electromechanical device of the sensor module to move the electromechanical device to generate a pressure wave in response to detection of the usage of the golf club,
wherein a parameter of the pressure wave identifies the golf club.

16. The method of claim 15, wherein the output differentiates the golf club for which the pressure wave is generated from other golf clubs.

17. The method of claim 15, wherein the electromechanical device includes a speaker adapted to generate the pressure wave.

18. The method of claim 17, wherein generating the pressure wave includes generating the pressure wave at a frequency between approximately fifteen kilohertz and approximately twenty-five kilohertz.

19. The method of claim 15, wherein generating the pressure wave includes generating the pressure wave at a frequency that uniquely identifies the golf club.

20. The method of claim 15, wherein detecting whether the impact corresponds to a golf shot or a false positive includes detecting a change in acceleration of the golf club.

21. A system for monitoring activity associated with a golf club, the system comprising:
(a) a sensor module affixed to or embedded in the golf club, the sensor module including:
sensor circuitry including at least one sensor that is operable to generate one or more outputs in response to usage of the golf club;
an electromechanical device operable to generate a pressure wave that propagates through air; and
first control circuitry, the first control circuitry being operatively coupled to the sensor circuitry and the electromechanical device, the first control circuitry being configured to (i) detect the usage of the golf club based on the one or more outputs of the sensor circuitry, and (ii) control the electromechanical device to move the electromechanical device to generate the pressure wave in response to detection of the usage of the golf club;
(b) an electronic device spaced away from the sensor module, the electronic device including:
an electroacoustic transducer operable to sense the pressure wave propagating through air and convert the pressure wave into an electrical signal; and
second control circuitry operable to (i) receive the electrical signal from the electroacoustic transducer, (ii) associate the pressure wave with the golf club based on a parameter of the pressure wave represented via the electrical signal, and (iii) attribute the usage of the golf club to the golf club.

22. The system of claim 21, wherein the output differentiates the golf club for which the pressure wave is generated from other golf clubs.

23. The system of claim 21, wherein the electronic device demodulates the electrical signal.

\* \* \* \* \*